United States Patent
Chappell et al.

(10) Patent No.: US 7,807,702 B2
(45) Date of Patent: Oct. 5, 2010

(54) SUBSTITUTED THIOPHENE CARBOXYLIC AMIDE GLUCAGON RECEPTOR ANTAGONISTS, PREPARATION AND THERAPEUTIC USES

(75) Inventors: Mark Donald Chappell, Noblesville, IN (US); Scott Eugene Conner, Indianapolis, IN (US); Philip-Arthur Hipskind, New Palestine, IN (US); Allie Edward Tripp, Indianapolis, IN (US); Guoxin Zhu, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 120 days.

(21) Appl. No.: 12/094,406

(22) PCT Filed: Nov. 21, 2006

(86) PCT No.: PCT/US2006/061132

§ 371 (c)(1),
(2), (4) Date: May 21, 2008

(87) PCT Pub. No.: WO2007/120284

PCT Pub. Date: Oct. 25, 2007

(65) Prior Publication Data

US 2008/0300289 A1 Dec. 4, 2008

Related U.S. Application Data

(60) Provisional application No. 60/739,692, filed on Nov. 23, 2005.

(51) Int. Cl.
*A61K 31/41* (2006.01)
*C07D 257/04* (2006.01)

(52) U.S. Cl. ...................... 514/381; 548/250
(58) Field of Classification Search ........... 514/381; 548/250

See application file for complete search history.

(56) References Cited

U.S. PATENT DOCUMENTS 5,811,459 A 9/1998 Breault et al.

FOREIGN PATENT DOCUMENTS

| WO | WO 03/048109 A | 6/2003 |
|----|----------------|--------|
| WO | WO 03/048109 | * 12/2003 |
| WO | WO2004/002480 | 1/2004 |
| WO | WO 2004/056763 A | 7/2004 |
| WO | WO 2006/102067 A | 9/2006 |

OTHER PUBLICATIONS

Kurukulasuriya, Ravi et al. "Biaryl amide glucagon receptor antagonists" *Bioorganic & Medicinal Chemistry Letters*, 14(9), p. 2049; table 1; 2004.

Beasley, Helen L. et al. "Development of a Panel of Immunoassays for Monitory DDT, Its Metabolites, and Analogs in Food and Environmental Matrixes" *Journal of Agricultural and Food Chemistry*, 46(8), pp. 3339-3352; compound Hapten VI, 1998.

Kundu, B. et al. "Identification of novel.alpha.-glucosidase inhibitors by screening libraries based on N-'r-(Benzyloxy) benzoyl! alanine derivatives" *Chemical Abstratcts Service*, 5(7), pp. 545-550, 2002.

* cited by examiner

*Primary Examiner*—Susannah Chung
(74) *Attorney, Agent, or Firm*—Dan L. Wood

(57) ABSTRACT

The present invention discloses novel compounds of Formula (I), or pharmaceutically acceptable salts thereof, which have glucagon receptor antagonist or inverse agonist activity, as well as methods for preparing such compounds. In another embodiment, the invention discloses pharmaceutical compositions comprising compounds of Formula (I) as well as methods of using them to treat diabetic and other glucagon related metabolic disorders, and the like.

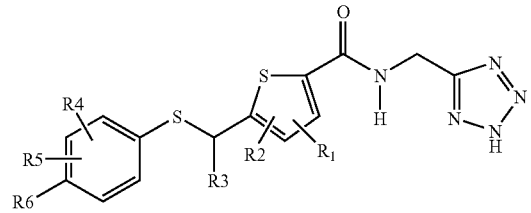

(I)

8 Claims, No Drawings

SUBSTITUTED THIOPHENE CARBOXYLIC AMIDE GLUCAGON RECEPTOR ANTAGONISTS, PREPARATION AND THERAPEUTIC USES

This is the national phase application, under 35 USC 371, for PCT/US2006/061132, filed Nov. 21, 2006, which claims the benefit, under 35 USC 119(e), of U.S. provisional application 60/739,692 filed Nov. 23, 2005.

This invention relates to compounds that are antagonists or inverse agonists of the glucagon receptor, and to pharmaceutical compositions thereof, and the uses of these compounds and compositions in the treatment of the human or animal body. The present compounds show a high affinity and selective binding for the glucagon receptor, and as such are useful in the treatment of disorders responsive to the modulation of glucagon receptors, such as diabetic and other glucagon related metabolic disorders, and the like.

Glucagon is a key hormonal agent that, in cooperation with insulin, mediates homeostatic regulation of the amount of glucose in the blood. Glucagon primarily acts by stimulating certain cells (important among these are liver cells) to release glucose when blood glucose levels fall. The action of glucagon is opposite to that of insulin, which stimulates cells to take up and store glucose whenever blood glucose levels rise. Both glucagon and insulin are peptide hormones. Glucagon is produced in the alpha islet cells of the pancreas and insulin is produced in the beta islet cells. Glucagon exerts its action by binding to and activating its receptor, which is a member of the Glucagon-Secretin branch of the 7-transmembrane G-protein coupled receptor family. The receptor functions by activating the adenylyl cyclase second messenger system resulting in an increase in cAMP levels. The glucagon receptor, or naturally occurring variants of the receptor, may possess intrinsic constitutive activity, in vitro, as well as in vivo (i.e. activity in the absence of an agonist). Compounds acting as inverse agonists can inhibit this activity. Diabetes mellitus is a common disorder of glucose metabolism. The disease is characterized by hyperglycemia and may be classified as type 1 diabetes, the insulin-dependent form, or type 2 diabetes, which is non-insulin-dependent in character. Subjects with type 1 diabetes are hyperglycemic and hypoinsulinemic, and the conventional treatment for this form of the disease is to provide insulin. However, in some patients with type 1 or type 2 diabetes, absolute or relative elevated glucagon levels have been shown to contribute to the hyperglycemic state. Both in healthy control animals as well as in animal models of type 1 and type 2 diabetes, removal of circulating glucagon with selective and specific antibodies has resulted in reduction of the glycemic level. Mice with a homozygous deletion of the glucagon receptor exhibit increased glucose tolerance. Also, inhibition of glucagon receptor expression using antisense oligonucleotides ameliorates diabetic syndrome in db/db mice. These studies suggest that glucagon suppression or an action that antagonizes glucagon could be a useful adjunct to conventional treatment of hyperglycemia in diabetic patients. The action of glucagon can be suppressed by providing an antagonist or an inverse agonist, i.e. substances that inhibit or prevent constitutive, or glucagon-induced, glucagon receptor mediated responses.

Several publications disclose peptides that are stated to act as glucagon antagonists. Peptide antagonists of peptide hormones are often potent; however they are generally known not to be orally available because of degradation by physiological enzymes and poor distribution in vivo. Therefore, orally available non-peptide antagonists of peptide hormones are generally preferred.

A number of publications have appeared in recent years reporting non-peptide agents that act at the glucagon receptor. For example, WO 03/048109, WO 2004/002480, and Kurukulasuriya et al., "Biaryl amide glucagon receptor antagonists" *Bioorganic & Medicinal Chemistry Letters*, vol. 14, no. 9, pages 2047-2050, 2004, each disclose non-peptide compounds allegedly having glucagon receptor antagonist activity. In spite of the number of treatments for diseases that involve glucagon, the current therapies suffer from one or more inadequacies, including poor or incomplete efficacy, unacceptable side effects, and contraindications for certain patient populations. Thus, there remains a need for an improved treatment using alternative or improved pharmaceutical agents that modulate glucagon receptor activity and treat the diseases that could benefit from glucagon receptor modulation. The present invention provides such a contribution to the art based on the finding that a novel class of compounds has a high affinity, selective, and potent inhibitory activity at the glucagon receptor. The present invention is distinct in the particular structures and their activities.

SUMMARY OF THE INVENTION

The present invention provides a compound structurally represented by Formula I:

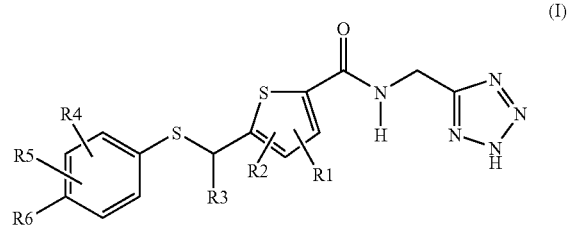

or a pharmaceutically acceptable salt thereof wherein:

R1 and R2 are independently —H or -halogen;

R3 is
—($C_1$-$C_8$) alkyl(optionally substituted with 1 to 3 halogens), —($C_3$-$C_7$)cycloalkyl,
—($C_1$-$C_6$)alkyl-($C_3$-$C_7$)cycloalkyl, or —($C_3$-$C_7$)cycloalkyl-($C_1$-$C_6$)alkyl(optionally substituted with 1 to 3 halogens);

R4 and R5 are independently
—H, -halogen, -hydroxy, hydroxymethyl, —CN, —($C_1$-$C_7$) alkoxy, —($C_2$-$C_7$)alkenyl, or
—($C_1$-$C_6$)alkyl (optionally substituted with 1 to 3 halogens);

R6 is

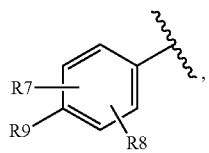

wherein the zig-zag mark shows the point of attachment to the parent molecule;

R7 and R8 are independently
—H, -halogen, —($C_1$-$C_6$)alkyl(optionally substituted with 1 to 3 halogens),
—($C_1$-$C_6$)alkoxy, —($C_3$-$C_7$)cycloalkyl, —C(O)R10, —COOR10, —OC(O)R10,
—OS(O)$_2$R10, —SR10, —S(O)R10, —S(O)$_2$R10, or —O($C_2$-$C_7$)alkenyl;

R9 is independently
—H, -halogen, —CN, —($C_3$-$C_7$)cycloalkyl, —C(O)R10, —COOR10, —OC(O)R10,
—OS(O)$_2$R10, —SR10, —S(O)R10, —S(O)$_2$R10, or —O($C_2$-$C_7$)alkenyl,
—($C_1$-$C_3$)alkoxy(optionally substituted with 1 to 3 halogens), or —($C_1$-$C_6$)alkyl (optionally substituted with 1 to 3 halogens); and R10 is independently at each occurrence
-hydrogen, or —($C_1$-$C_6$)alkyl(optionally substituted with 1 to 3 halogens).

The present invention provides compounds that are useful as glucagon receptor antagonists or inverse agonists. The present invention further provides compounds that are selective antagonists or inverse agonists of the glucagon receptor over the GLP-1 receptor. The present invention further provides a pharmaceutical composition which comprises a compound of Formula I, or a pharmaceutical salt thereof, and a pharmaceutically acceptable carrier, diluent, or excipient. The present invention further provides methods of using these compounds and compositions in the treatment of disorders responsive to the modulation of glucagon receptors, such as diabetic and other glucagon related metabolic disorders.

DETAILED DESCRIPTION OF THE INVENTION

In one embodiment, the present invention provides compounds of Formula I as described in detail herein. While all of the compounds of the present invention are useful, certain of the compounds are particularly interesting and are preferred. The following listing sets out several groups of preferred compounds. It will be understood that each of the listings may be combined with other listings to create additional groups of preferred embodiments as indicated herein.

In another embodiment the invention provides a compound of formula I wherein R1 and R2 are —H;

R3 is
—($C_1$-$C_8$)alkyl(optionally substituted with 1 to 3 halogens), —($C_3$-$C_6$)cycloalkyl,
—($C_1$-$C_6$)alkyl-($C_3$-$C_6$)cycloalkyl, or —($C_3$-$C_6$)cycloalkyl-($C_1$-$C_6$)alkyl(optionally substituted with 1 to 3 halogens);

R4 and R5 are independently
—H, -halogen, or —($C_1$-$C_6$)alkyl (optionally substituted with 1 to 3 halogens);

R6 is

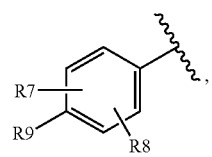

wherein the zig-zag mark shows the point of attachment to the parent molecule;

R7 and R8 are independently
—H, -halogen, —($C_1$-$C_3$)alkyl(optionally substituted with 1 to 3 halogens), or
—($C_1$-$C_3$)alkoxy; and R9 is independently
—H, halogen, or —($C_1$-$C_6$)alkyl (optionally substituted with 1 to 3 halogens).

In another embodiment the invention provides a compound of formula I wherein R1 and R2 are —H;

R3 is
—($C_1$-$C_8$)alkyl(optionally substituted with 1 to 3 halogens), —($C_3$-$C_6$)cycloalkyl,
—($C_1$-$C_6$)alkyl-($C_3$-$C_6$)cycloalkyl, or —($C_3$-$C_6$)cycloalkyl-($C_1$-$C_6$)alkyl(optionally substituted with 1 to 3 halogens);

R4 and R5 are independently
—H, -halogen, or —CH$_3$ (optionally substituted with 1 to 3 halogens);

R6 is

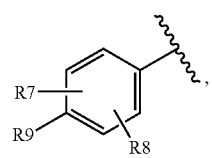

wherein the zig-zag mark shows the point of attachment to the parent molecule;

R7 and R8 are independently —H, or -halogen; and

R9 is independently —($C_1$-$C_6$)alkyl (optionally substituted with 1 to 3 halogens).

In another embodiment the invention provides a compound of formula I wherein

R1 and R2 are —H; R3 is —($C_1$-$C_8$)alkyl(optionally substituted with 1 to 3 halogens), —($C_3$-$C_6$)cycloalkyl, —($C_1$-$C_6$) alkyl-($C_3$-$C_6$)cycloalkyl, or —($C_3$-$C_6$)cycloalkyl-($C_1$-$C_6$) alkyl(optionally substituted with 1 to 3 halogens); R4 and R5 are —CH$_3$ (optionally substituted with 1 to 3 halogens) and each occupies a position adjacent to R6 on the phenyl ring to which R6 is attached;

R6 is

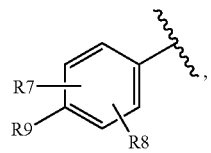

wherein the zig-zag mark shows the point of attachment to the parent molecule;

R7 and R8 are —H; and R9 is independently —($C_1$-$C_6$)alkyl (optionally substituted with 1 to 3 halogens).

In another embodiment the invention provides a compound of Formula I wherein R1 and R2 are independently hydrogen or halogen; R3 is methyl, ethyl, propyl, isopropyl, butyl, pentyl, hexyl, heptyl, octyl, 3,3-dimethylbutyl, 2-methylpropyl, 3-methyl-butyl, tertbutyl, 4-methylpentyl, 2,2-dimethylpropyl, 3,3,3-trifluoropropyl, 4,4,4-trifluorbutyl, cyclopropyl, cyclobutyl, cyclopentyl, or cyclohexyl; R4 and R5 are independently hydrogen, methyl, ethyl, tertbutyl, cyclohexyl, pentyl, isopropoxy, chloro, fluoro, bromo, hydroxy, trifluoromethyl, —CN, methoxy, hydroxymethyl, 4-methylpentyloxy, or pentyloxy; R7 and R8 are independently hydrogen, fluoro, chloro, methyl, ethyl, pentyl, isopropyl, tertbutyl, trifluoromethyl, acetyl, 2-methylpropyl, methoxy, cyclohexyl, or trifluoromethoxy; R9 is hydrogen, bromo, fluoro, methyl, tertbutyl, trifluoromethyl, or isopropyl.

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably R1 is —H. Preferably R1 is fluorine. Preferably R1 is chlorine. Preferably R2 is —H. Preferably R2 is fluorine. Preferably R2 is chlorine. Preferably R1 and R2 are —H. Preferably R1 is fluorine and R2 is fluorine.

Preferably R3 is —($C_1$-$C_8$)alkyl(optionally substituted with 1 to 3 halogens). Preferably R3 is ethyl, propyl, isopropyl, butyl, tertbutyl, 3-methyl-butyl, pentyl, hexyl, heptyl, octyl, 3,3-dimethylbutyl, 2-methylpropyl, 4-methylpentyl, 2,2-dimethylpropyl, 3,3,3-trifluoropropyl, or 4,4,4-trifluorbutyl. Preferably R3 is isopropyl, butyl, tertbutyl, 3-methylbutyl, pentyl, 3,3-dimethylbutyl, 2-methylpropyl, 4-methylpentyl, 2,2-dimethylpropyl, 3-trifluoropropyl, or 4,4,4-trifluorbutyl. Preferably R3 is isopropyl, 3-methyl-butyl, trifluoropropyl, or 4,4,4-trifluorbutyl.

Preferably R3 is —($C_3$-$C_7$)cycloalkyl. Preferably R3 is cyclopropyl, cyclobutyl, cyclopentyl, or cyclohexyl. Preferably R3 is cyclopropyl. Preferably R3 is cyclobutyl. Preferably R3 is cyclopentyl. Preferably R3 is cyclohexyl.

Preferably R3 is —($C_1$-$C_6$)alkyl-($C_3$-$C_7$)cycloalkyl. Preferably R3 is —($C_1$-$C_3$)alkyl-($C_3$-$C_6$)cycloalkyl. Preferably R3 is —($C_1$-$C_3$)alkyl-cyclopropyl. Preferably R3 is —($C_1$-$C_3$)alkyl-cyclobutyl. Preferably R3 is —($C_1$-$C_3$)alkyl-cyclopentyl. Preferably R3 is —($C_1$-$C_3$)alkyl-cyclohexyl.

Preferably R3 is —($C_3$-$C_7$)cycloalkyl-($C_1$-$C_6$)alkyl(optionally substituted with 1 to 3 halogens). Preferably R3 is -cyclopropyl-($C_1$-$C_6$)alkyl(optionally substituted with 1 to 3 halogens). Preferably R3 is -cyclobutyl-($C_1$-$C_6$)alkyl(optionally substituted with 1 to 3 halogens). Preferably R3 is -cyclopentyl-($C_1$-$C_6$)alkyl(optionally substituted with 1 to 3 halogens). Preferably R3 is -cyclohexyl-($C_1$-$C_6$)alkyl(optionally substituted with 1 to 3 halogens).

Preferably R4 is —H, -halogen, -hydroxy, hydroxymethyl, or —($C_1$-$C_6$)alkyl (optionally substituted with 1 to 3 halogens). Preferably R4 is —H, -halogen, or —($C_1$-$C_3$)alkyl (optionally substituted with 1 to 3 halogens). Preferably R4 is —H, -halogen, or —$CH_3$. Preferably R4 is —H. Preferably R4 is fluorine, chlorine, or bromine. Preferably R4 is —$CH_3$.

Preferably R5 is —H, -halogen, -hydroxy, hydroxymethyl, or —($C_1$-$C_6$)alkyl (optionally substituted with 1 to 3 halogens). Preferably R5 is —H, -halogen, or —($C_1$-$C_3$)alkyl (optionally substituted with 1 to 3 halogens). Preferably R5 is —H, -halogen, or —$CH_3$. Preferably R5 is —H. Preferably R5 is fluorine, chlorine, or bromine. Preferably R5 is —$CH_3$.

Preferably R4 and R5 are —H. Preferably R4 is halogen and R5 is —H. Preferably R4 is —H and R5 is —$CH_3$. Preferably R4 and R5 are —$CH_3$. Preferably R4 and R5 are —$CH_3$ and each occupies a position adjacent to R6 on the phenyl ring to which R6 is attached.

Preferably R7 is -halogen, —($C_1$-$C_6$)alkyl(optionally substituted with 1 to 3 halogens), —($C_1$-$C_6$)alkoxy, —($C_3$-$C_7$)cycloalkyl, —C(O)R10, —COOR10, —OC(O)R10, —OS(O)$_2$R10, —SR10, —S(O)R10, —S(O)$_2$R10, or —O($C_2$-$C_7$)alkenyl. Preferably R7 is -halogen, —($C_1$-$C_6$)alkyl (optionally substituted with 1 to 3 halogens), or —($C_1$-$C_6$)alkoxy. Preferably R7 is —H or -halogen. Preferably R7 is —H.

Preferably R8 is -halogen, —($C_1$-$C_6$)alkyl(optionally substituted with 1 to 3 halogens), —($C_1$-$C_6$)alkoxy, —($C_3$-$C_7$)cycloalkyl, —C(O)R10, —COOR10, —OC(O)R10, —OS(O)$_2$R10, —SR10, —S(O)R10, —S(O)$_2$R10, or —O($C_2$-$C_7$)alkenyl. Preferably R8 is -halogen, —($C_1$-$C_6$)alkyl (optionally substituted with 1 to 3 halogens), or —($C_1$-$C_6$)alkoxy. Preferably R8 is —H or -halogen. Preferably R8 is —H. Preferably R7 is —H and R8 is —H.

Preferably R9 is —($C_1$-$C_6$)alkyl (optionally substituted with 1 to 3 halogens). Preferably R9 is methyl, ethyl, propyl, isopropyl, butyl, tertbutyl, trifluoromethyl, 3-methyl-butyl, pentyl, hexyl, 3,3-dimethylbutyl, 2-methylpropyl, 4-methylpentyl, 2,2-dimethylpropyl, 3-trifluoropropyl, or 4-trifluorbutyl. Preferably R9 is isopropyl, tertbutyl, or trifluoromethyl.

Preferably R7 is —H, R8 is —H, and R9 is isopropyl, tertbutyl, or trifluoromethyl.

Preferably R10 is independently at each occurrence —($C_1$-$C_6$)alkyl(optionally substituted with 1 to 3 halogens).

Further embodiments of the invention include the compounds of formulae X1 to X11. A further embodiment of the invention are any novel intermediate preparations described herein which are useful for preparing the glucagon receptor antagonists or inverse agonists of formulae I, or X1 to X11.

TABLE 1

| Formula Number | Structure |
|---|---|
| X1 | 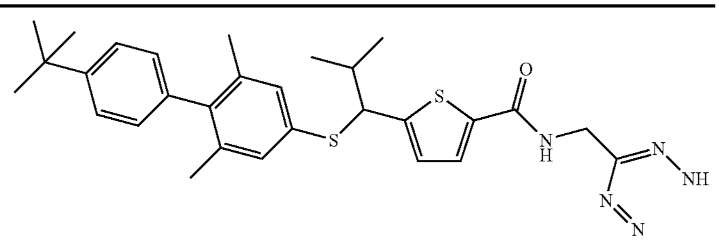 |
| X2 | 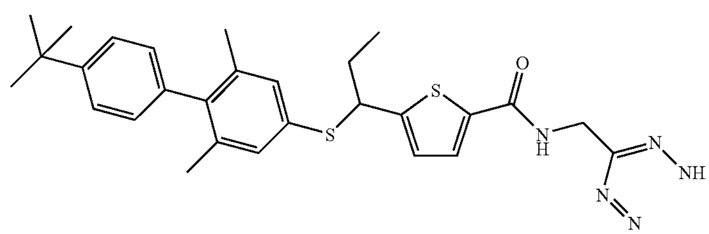 |
| X3 | 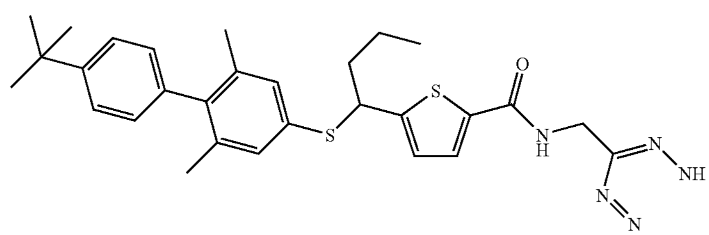 |
| X4 | 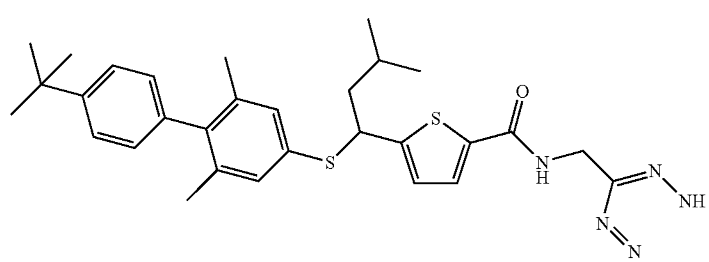 |
| X5 | 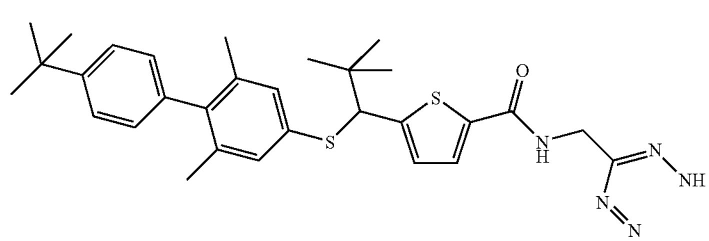 |

TABLE 1-continued

| Formula Number | Structure |
|---|---|
| X6 | 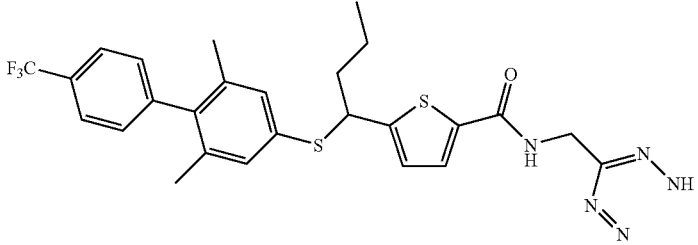 |
| X7 | 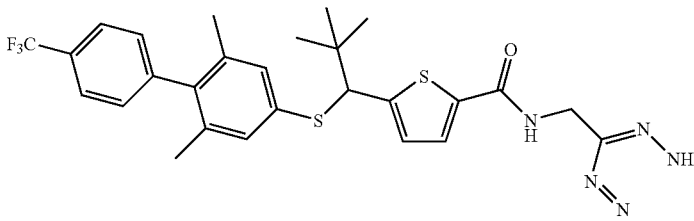 |
| X8 | 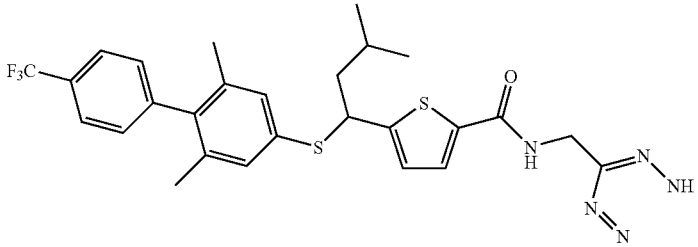 |
| X9 | 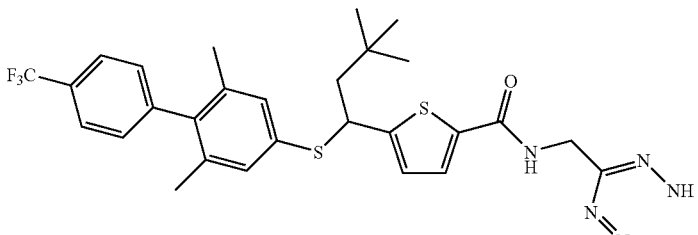 |
| X10 | 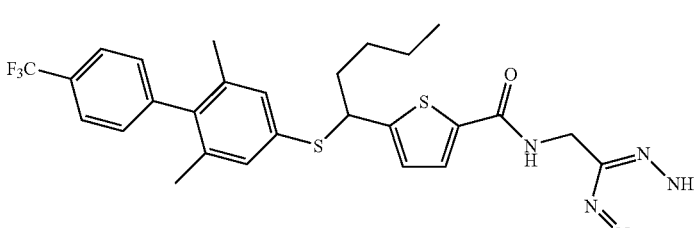 |
| X11 | 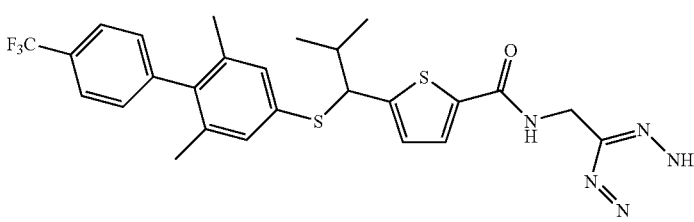 |

Due to their interaction with the glucagon receptor, the present compounds are useful in the treatment of a wide range of conditions and disorders in which an interaction with the glucagon receptor is beneficial. These disorders and conditions are defined herein as "diabetic and other glucagon related metabolic disorders". One of skill in the art is able to identify "diabetic and other glucagon related metabolic disorders" by the involvement of glucagon receptor mediated signaling either in the pathophysiology of the disorder, or in the homeostatic response to the disorder. Thus, the compounds may find use for example to prevent, treat, or alleviate, diseases or conditions or associated symptoms or sequelae, of the endocrinological system, the central nervous system, the peripheral nervous system, the cardiovascular system, the pulmonary system, and the gastrointestinal system, while reducing and or eliminating one or more of the unwanted side effects associated with the current treatments. "Diabetic and other glucagon related metabolic disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrythmia, premature death, anti-apoptosis, wound healing, impaired glucose tolerance (IGT), insulin resistance syndromes, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting the glucagon receptor; for use in inhibiting a glucagon receptor mediated cellular response in a mammal; for use in reducing the glycemic level in a mammal; for use in treating a disease arising from excessive glucagon; for use in treating diabetic and other glucagon related metabolic disorders in a mammal; and for use in treating diabetes, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting the glucagon receptor; for the manufacture of a medicament for inhibiting a glucagon receptor mediated cellular response in a mammal; for the manufacture of a medicament for reducing the glycemic level in a mammal; for the manufacture of a medicament for treating a disease arising from excessive glucagon; for the manufacture of a medicament for treating diabetic and other glucagon related metabolic disorders in a mammal; and for the manufacture of a medicament for preventing or treating diabetes, obesity, hyperglycemia, atherosclerosis, ischemic heart disease, stroke, neuropathy, and improper wound healing.

The present invention further provides a method of treating conditions resulting from excessive glucagon in a mammal; a method of inhibiting the glucagon receptor in a mammal; a method of inhibiting a glucagon receptor mediated cellular response in a mammal; a method of reducing the glycemic level in a mammal; a method of treating diabetic and other glucagon related metabolic disorders in a mammal; a method of preventing or treating diabetes, obesity, hyperglycemia, atherosclerosis, ischemic heart disease, stroke, neuropathy, and improper wound healing; said methods comprising administering to a mammal in need of such treatment a glucagon receptor-inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting the glucagon receptor; adapted for use in inhibiting glucagon receptor mediated cellular responses; adapted for use in reducing the glycemic level in a mammal; adapted for use in treating diabetic and other glucagon related metabolic disorders in a mammal; and adapted for use in preventing or treating diabetes, obesity, hyperglycemia, atherosclerosis, ischemic heart disease, stroke, neuropathy, and wound healing.

The compound or salt of the present invention further provides a diagnostic agent for identifying patients having a defect in the glucagon receptor, as a therapy to increase gastric acid secretions, and to reverse intestinal hypomobility due to glucagon administration. The invention also provides a method for the treatment of disorders or diseases, wherein a glucagon antagonistic action is beneficial, the method comprising administering to a subject in need thereof an effective amount of a compound according to the invention. In another embodiment of the invention, the present compounds are used for the preparation of a medicament for the treatment of any glucagon-mediated conditions and diseases. In another embodiment of the invention, the present compounds are used for the preparation of a medicament for the treatment of hyperglycemia. In yet another embodiment of the invention, the present compounds are used for the preparation of a medicament for lowering blood glucose in a mammal. The present compounds are effective in lowering the blood glucose, both in the fasting and the postprandial stage. In still another embodiment of the invention, the present compounds are used for the preparation of a pharmaceutical composition for the treatment of IGT. In a further embodiment of the invention, the present compounds are used for the preparation of a pharmaceutical composition for the treatment of type 2 diabetes. In yet a further embodiment of the invention the present compounds are used for the preparation of a pharmaceutical composition for the delaying or prevention of the progression from IGT to type 2 diabetes. In yet another embodiment of the invention the present compounds are used for the preparation of a pharmaceutical composition for the delaying or prevention of the progression from non-insulin requiring type 2 diabetes to insulin requiring type 2 diabetes. In a further embodiment of the invention the present compounds are used for the preparation of a pharmaceutical composition for the treatment of type 1 diabetes. Such treatment is normally accompanied by insulin therapy. In yet a further embodiment of the invention the present compounds are used for the preparation of a pharmaceutical composition for the treatment of obesity. In still a further embodiment of the invention the present compounds are used for the preparation of a pharmaceutical composition for the treatment of disorders of the lipid metabolism. In still another embodiment of the invention the present compounds are used for the preparation of a pharmaceutical composition for the treatment of an appetite regulation or energy expenditure disorder. In a further embodiment of the invention, treatment of a patient with the present compounds is combined with diet and/or exercise.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $Asp^{B28}$ human insulin, U.S. Pat. No. 5,504,188 (Eli Lilly), for example $Lys^{B28}$ $Pro^{B29}$ human insulin, EP 368 187 (Aventis), for example Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In another embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide, for example, metformin.

In yet another embodiment of the invention the present compounds are administered in combination with a meglitinide, for example, repaglinide or nateglinide.

In still another embodiment of the invention the present compounds are administered in combination with a thiazolidinedione insulin sensitizer, for example, troglitazone, ciglitazone, pioliatazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor, for example, voglibose, emiglitate, miglitol or acarbose.

In another embodiment of the invention the present compounds are administered in combination with an agent acting on the ATP-dependent potassium channel of the β-cells, for example, tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further embodiment of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140 MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant). In another embodiment the antiobesity agent is dexamphetamine or amphetamine. In another embodiment the antiobesity agent is leptin. In another embodiment the antiobesity agent is fenfluramine or exfenfluramine. In still another embodiment the antiobesity agent is sibutramine. In a further embodiment the antiobesity agent is orlistat. In another embodiment the antiobesity agent is mazindol or phentermine. In still another embodiment the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolol, timolol, pindolol, propranolol and metoprolol, SCE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitor, imidazolines, 11-β-hydroxysteroid dehydrogenase inhibitors, lipoprotein lipase activator, AMPK activators, immunosuppresive drugs, nicotinamide, ASIS, anti-androgens or carboxypeptidase inhibitors.

It should be understood that any suitable combination of the compounds according to the invention with diet and/or exercise, one or more of the above-mentioned compounds are considered to be within the scope of the present invention.

General terms used in the description of compounds, compositions, and methods herein described, bear their usual meanings. Throughout the instant application, the following terms have the indicated meanings:

"GLP-1" means glucagon-like peptide 1. The term "glucagon receptor" means one or more receptors that interact specifically with glucagon to result in a biological signal. The term "GLP-1 receptor" means one or more receptors that interact specifically with glucagon-like peptide 1 to result in a biological signal.

The term "glucagon receptor antagonist" means a compound of the present invention with the ability to block cAMP production in response glucagon. The term "glucagon receptor inverse agonist" means a compound of the present invention with the ability to inhibit the constitutive activity of glucagon receptor. The term "selective" antagonist or inverse agonist means a compound having greater affinity for the glucagon receptor as compared to the affinity for the GLP-1 receptor.

In the general formulae of the present document, the general chemical terms have their usual meanings. For example;

"Halogen" or "halo" means fluoro, chloro, bromo and iodo.

The term "alkyl," unless otherwise indicated, refers to those alkyl groups of a designated number of carbon atoms of either a straight or branched saturated configuration. As used herein, "($C_1$-$C_3$)alkyl" are one to three carbon atoms, such as methyl, ethyl, propyl, n-propyl, isopropyl, and the like and branched or isomeric forms thereof, and optionally may be substituted with one to three halogens or a designated number of substituents as set forth in the embodiments recited herein. "($C_1$-$C_6$)alkyl" are one to six carbon atoms such as methyl, ethyl, propyl, n-propyl, isopropyl, n-butyl, isobutyl, sec-butyl and tert-butyl, pentyl, isopentyl, hexyl, and the like, and branched or isomeric forms thereof, and optionally may be substituted with one to three halogens or a designated number of substituents as set forth in the embodiments recited herein. "($C_1$-$C_8$) alkyl" are one to eight carbon atoms, such as methyl, ethyl, propyl, butyl, pentyl, hexyl, heptyl, octyl, and the like, and branched or isomeric forms thereof, and optionally may be substituted with one to three halogens as set forth in the embodiments recited herein.

The term "($C_3$-$C_7$) cycloalkyl" refers to a saturated or partially saturated carbocycle containing one or more rings of from 3 to 7 carbon atoms. Examples of ($C_3$-$C_7$) cycloalkyl include but are not limited to cyclopropyl, cyclobutyl, cyclopentyl, cyclohexyl and cycloheptyl. The term "($C_3$-$C_6$) cycloalkyl" refers to a saturated carbocycle ring of from 3 to 6 carbon atoms. Examples of ($C_3$-$C_6$) cycloalkyl include but are not limited to cyclopropyl, cyclobutyl, cyclopentyl, and cyclohexyl.

The term "($C_1$-$C_3$) alkoxy" represents an alkyl group of one to three carbon atoms attached through an oxygen bridge, such as methoxy, ethoxy, propoxy, and the like. The term "($C_1$-$C_6$) alkoxy" represents an alkyl group of one to six carbon atoms attached through an oxygen bridge, such as methoxy, ethoxy, propoxy, isopropoxy, butoxy, tert-butoxy, pentoxy, and the like. The term "($C_1$-$C_7$) alkoxy" represents an alkyl group of one to seven carbon atoms attached through an oxygen bridge, such as methoxy, ethoxy, propoxy, isopropoxy, butoxy, tert-butoxy, pentoxy, and the like, and may be optionally substituted with three halogens as set forth in the embodiments recited herein.

The term "($C_2$-$C_7$) alkenyl" means hydrocarbon chain of two to seven carbon atoms of either a straight or branched configuration having at least one carbon-carbon double bond which may occur at any point along the chain, such as ethenyl, propenyl, butenyl, pentenyl, vinyl, alkyl, 2-butenyl and the like, and may be optionally substituted with one to three halogens as set forth in the embodiments recited herein.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The term "a glucagon receptor mediated cellular response" includes various responses by mammalian cells to glucagon stimulation or glucagon receptor activity. For example "glucagon receptor mediated cellular responses," include but are not limited to, release of glucose from liver, or other cells, in response to glucagon stimulation or glucagon receptor activity. One of ordinary skill in the art can readily identify other cellular responses mediated by glucagon receptor activity, for example by observing a change in the responsive cellular endpoint after contacting the cell with an effective dose of glucagon.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The compounds of the present invention may be chiral, and it is intended that any enantiomers, whether pure, partially purified, or racemic mixtures, are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. The invention also includes tautomers, enantiomers and other stereoisomers of the compounds of Formula I. Such variations are contemplated to be within the scope of the invention.

The compounds of Formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I, can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen," *Stereochemistry of Organic Compounds*," (Wiley-Interscience 1994), and European Patent Application No. EP-A-838448, published Apr. 29, 1998. Examples of resolutions include recrystallization techniques or chiral chromatography. Unless otherwise indicated, a compound indicated to be "isomer 1" will be the first isomer eluted from the chiral separation column and "isomer 2" will be the second.

In general, the term "pharmaceutical" when used as an adjective means substantially non-toxic to living organisms. For example, the term "pharmaceutical salt" as used herein, refers to salts of the compounds of Formula I, which are substantially non-toxic to living organisms. The present invention also encompasses pharmaceutically acceptable salts of the present compounds. Pharmaceutically acceptable salts and common methodology for preparing them are well known in the art. See e.g., P. Stahl, et al., "Handbook Of Pharmaceutical Salts: Properties, Selection, and Use,"

(VCHA/Wiley-VCH, 2002); Berge, S. M, Bighley, L. D., and Monkhouse, D. C., "Pharmaceutical Salts," *J. Pharm. Sci.,* 66:1, 1977.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into a compound of the present invention. Conventional procedures for the selection and preparation of suitable prodrug derivatives are described, for example in "Design of Prodrugs", ed. H. Bundgaard, Elsevier, 1985.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "psi" refers to pounds per square inch; "min" refers to minutes; "h" or "hr" refers to hours; "TLC" refers to thin layer chromatography; "HPLC" refers to high performance liquid chromatography; "R$_f$" refers to retention factor; "R$_t$" refers to retention time; "δ" refers to part per million down-field from tetramethylsilane; "MS" refers to mass spectrometry; "MS (ES)" refers to electron spray mass spectrometry, "UV" refers to ultraviolet spectrometry; "$^1$H NMR" refers to proton nuclear magnetic resonance spectrometry. In addition; "RT" refers to room temperature; "DEAD" refers to diethylazodicrboxylate; "PPh$_3$" refers to triphenylphosphine; "ADDP" refers to 1,1'-(azodicarbonyl)dipiperidine; "PBu$_3$" refers to tributylphosphine; "OTF" refers to triflate; "LAH" refers to lithium aluminum hydride; "DIBAL-H" refers to diisobutylaluminum hydride; "KOtBu" refers to potassium t-butoxide; "THF" refers to tetrahydrofuran; "TBP" refers to tributylphosphine; "EDCI" refers to 1-(3-dimethylaminopropyl)-3-ethylcarbodiamide hydrochloride; "DMAP" refers to dimethylaminopyridine; "HNMe(OMe)" refers to N,N, dimethylhydroxyamine; "CDMT" refers to 2-chloro-4,6-dimethoxy-[1,3,5] triazine; "NMM" refers to N-methyl morpholine; "DCM" refers to dichloromethane; "DMSO" refers to dimethylsulfoxide; "ET$_3$N" refers to triethylamine; "DMF" refers to dimethylformamide; "PBr$_3$" refers to phosphorus tribromide; "Et" in a formula refers to ethyl, for example Et$_2$O refers to diethylether, and EtOAc refers to ethylacetate; "PyBOP" refers to bromo-tris-pyrrolidino-phosphonium hexafluorophosphate; "Me" refers to methyl as in MeOH which is methanol; "Pd/C" refers to 10% palladium on carbon. Unless otherwise indicated, isomer 1 refers to the first isomer to be eluted in a chiral separation and isomer 2 refers to the second isomer to be eluted in a chiral separation.

General Schemes

All of the compounds of the present invention can be chemically prepared, for example, by following the synthetic routes set forth in the Schemes and/or the Preparations and Examples below. However, the following discussion is not intended to be limiting to the scope of the present invention in any way. For example, the specific synthetic steps for each of the routes described may be combined in different ways, or in conjunction with steps from different schemes, to prepare additional compounds of Formula I.

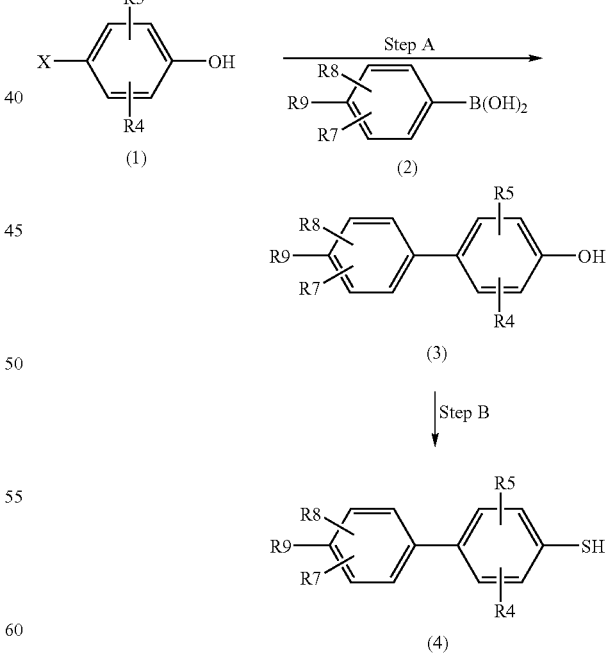

In Scheme I, Step A, a 4-halophenol of formula (1), (X=I or Br) is coupled with a phenyl boronic acid of formula (2), using a Suzuki reaction to provide a biphenyl hydroxy of formula (3). It will be recognized by one skilled in the art that such Suzuki couplings using aryl halides and phenyl boronic acids can be effected using a wide variety of reaction conditions. Preferred conditions use oxydi-2,1-phenylene)bis(diphenylphosphine) in the presence of palladium acetate and potassium fluoride, in an inert solvent, such as tetrahydrofuran. The reaction is heated at a temperature of 50° C. to the reflux temperature of the solvent for about 4 to 48 hours under nitrogen.

Alternatively the Suzuki reaction may be effected using tetrakis(triphenylphosphine)palladium with potassium fluoride under nitrogen. The reaction proceeds in an inert solvent such as toluene or benzene and water at a temperature of 40° C. to the reflux temperature of the reaction for about 4 to 48 hours In Scheme I, Step B, a biphenyl hydroxy of formula (3) is coupled with dimethylthiocarbamoyl chloride, undergoes a thermal rearrangement and subsequent solvolysis of the dimethyl-thiocarbamic acid ester intermediate to provide a biphenyl thiol of formula (4). The coupling reaction to give the thiocarbamate is accomplished in the presence of 4-dimethylaminopyridine with an organic amine such as triethylamine or diisopropylethylamine. The reaction is performed in an inert solvent such as dioxane, tetrahydrofuran, benzene or toluene, with dioxane being preferred at temperature of 65° C. to the reflux temperature of the solvent. The resulting thiocarbamate is thermally rearranged in tetradecane at a temperature of 200 to 250° C. with the preferred temperature being about 245° C. to give a dimethyl-thiocarbamic acid ester. Solvolysis with sodium methoxide in methanol or sodium ethoxide in ethanol gives the biphenyl thiol of formula (4).

Scheme II

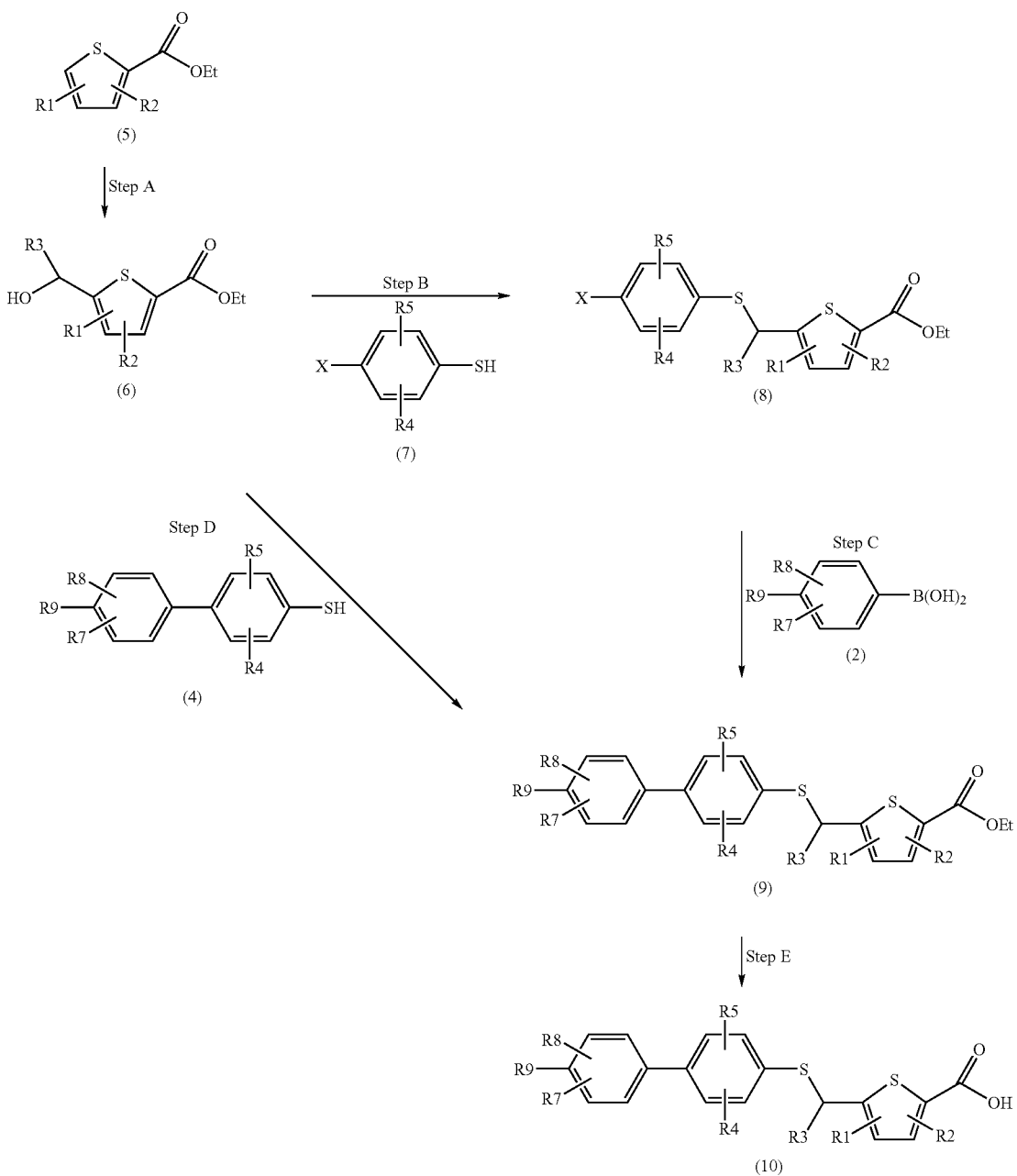

In Scheme II, Step A, an ethyl thiophene 2-carboxylate of formula (5) is alkylated with an aldehyde (R3CHO) to give a secondary alcohol of formula (6). An ethyl thiophene 2-carboxylate of formula (5) is treated with lithium diisopropylamide at a temperature of −80 to −70° C. and then treated with an aldehyde in an inert solvent such as tetrahydrofuran. The reaction is allowed to warm to ambient temperature over about 12 to 24 hours and the product is isolated using extractive techniques to give the secondary alcohol of formula (6).

In Scheme II, Step B, a secondary alcohol of formula (6) is coupled with a 4-halo thiophenol (X=Br or I) of formula (7), to give a 4-halophenyl thioether of formula (8). The coupling is effected with a Lewis acid, such as zinc iodide ($ZnI_2$), in an inert solvent such as dichloromethane or dichloroethane at a temperature of 0 to 50° C., with dichloroethane at room temperature being the preferred conditions. The product is isolated using common extractive techniques to give the 4-halophenyl thioether of formula (8).

Alternatively the coupling of the secondary alcohol and thiophenol may be affected using Mitsinobu conditions. Common redox systems, known to those skilled in the art, such as diethyl azodicarboxylate (DEAD)/triphenylphosphine, N,N,N',N'-tetramethylazodicarboxamide (TMAD)/tributylphosphine or 1,1'-(azodicarbonyl)dipiperidine (ADDP)/tributylphosphine may be used to effect the transformation.

In Scheme II, Step C, a 4-halophenyl thioether of formula (8), is coupled with a phenyl boronic acid of formula (2) in a Suzuki reaction to provide the biphenyl thioether of formula (9), using conditions as described for Scheme I, Step A.

Alternatively, in Scheme II, Step D, a biphenyl thiol of formula (3) is coupled using conditions described for Scheme II, Step B to give a biphenyl thioether of formula (9).

In Scheme II, Step E, the thiophene carboxylic acid ethyl ester of formula (9) is hydrolyzed to a thiophene carboxylic acid of formula (10). The ester is hydrolyzed in an appropriate water soluable solvent such as ethanol, methanol, dioxane, or tetrahydrofuran, with ethanol being preferred. The ester is treated with an inorganic base such as potassium or sodium hydroxide, with sodium hydroxide being preferred, at room temperature to the reflux temperature of the solvent for 2 to 48 hours. The thiophene carboxylic acid of formula (10) is isolated by neutralization with hydrochloric acid followed by common extractive techniques.

Scheme III

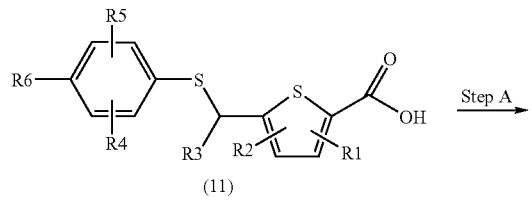

(11)

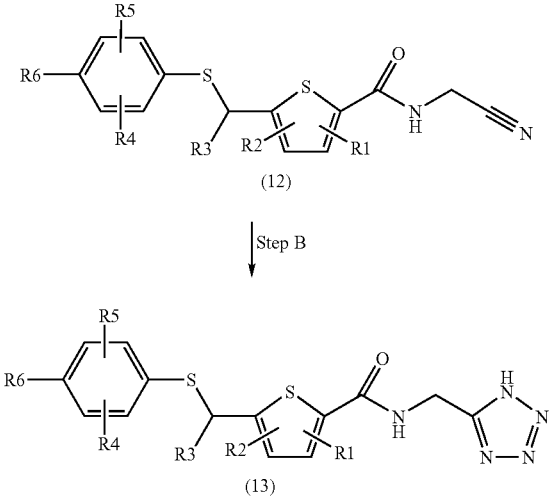

In Scheme III, Step A, a thiophene carboxylic acid of formula (11) is acylated to give an amide of formula (12). It will be recognized by one skilled in the art that there are numerous conditions for amide bond formation between a carboxylic acid and an amine. Such methods can be found in the text of R. C. Larock in "Comprehensive Organic Transformations", VCH Publishers, 1989, p. 972-976. The preferred conditions use a catalytic amount of 4-dimethylaminopyridine (DMAP), 1,[3-(dimethylamino)propyl]-3-ethylcarbodiimide hydrochloride (EDCI) and an organic base such as diisopropylethylamine or triethylamine in an inert solvent such as dichloromethane or tetrahydrofuran. The active ester is treated with aminoacetonitrile hydrochloride at 0° C. to the reflux temperature of the solvent, but preferably at room temperature, for about 4 to 48 hours.

Alternatively, In Scheme III, Step A, another set of preferred conditions use 2-chloro-4,6-dimethoxy-1,3,5-triazine to form the active ester in the presence of an organic base such as N-methyl morpholine in an inert solvent such as tetrahydrofuran. The active ester is treated with aminoacetonitrile hydrochloride at 0 to 50° C. for 4 to 48 hours to form the amide of formula (12).

In Scheme III, Step B, an amide of formula (12) is cyclized to a tetrazole of formula (13). It will be recognized by the skilled artisan that useful reagents for forming tetrazoles from nitriles include azidotrimethylsilane, azidotributyltin, and sodium azide. The preferred conditions use sodium azide in the presence of an alkyl amine hydrochloride such as triethylamine or diisopropylethylamine hydrochloride in an inert solvent such as toluene, benzene, dimethylformamide, tetrahydrofuran, or dioxane. The preferred conditions use toluene at a temperature of 40° C. to the reflux temperature of the solvent for a period of 4 to 48 hours. The product is isolated by acidification with aqueous hydrochloric acid and extraction into an appropriate organic solvent, such as ethyl acetate.

PREPARATIONS AND EXAMPLES

The Examples provided herein are illustrative of the invention claimed herein and are not intended to limit the scope of the claimed invention in any way. Names of the preparations and examples are derived using ChemDraw.

$^1$H NMR spectra are recorded on a Varian 400 MHz spectrometer at ambient temperature. Data are reported as follows: chemical shift in ppm from internal standard tetramethylsilane on the (scale, multiplicity (b=broad, s=singlet, d=doublet, t=triplet, q=quartet, qn=quintet and m=multiplet), integration, coupling constant (Hz) and assignment. $^1$H-NMR indicates a satisfactory NMR spectrum was obtained for the compound described. Monoisotopic mass spectral data are obtained on an Agilent G1956B MSD single quadrapole instrument using electrospray ionization (ESI or ES). Analytical thin layer chromatography is performed on EM Reagent 0.25 mm silica gel 60-F plates. Visualization is accomplished with UV light. All examples are racemic unless indicated otherwise.

Preparation 1

2,6-dimethyl-4'-(trifluoromethyl)biphenyl-4-ol

4-Bromo-3,5-dimethylphenol (115.00 g, 571.96 mmol), 4-(trifluoromethyl)phenyl boronic acid (130.36 g, 686.35 mmol), (oxydi-2,1-phenylene)bis(diphenylphosphine) (126.00 g, 233.96 mmol), potassium fluoride (99.69 g, 1.72 mol), and Pd(OAc)$_2$ (25.68 g, 114.39 mmol) are added to nitrogen-sparged tetrahydrofuran (3.0 L) and heated to reflux. The consumption of the starting material, 4-bromo-3,5-dimethylphenol, is monitored by GC. Reflux is maintained until 4-bromo-3,5-dimethylphenol has been consumed and is generally complete after 18 h. After the reaction is complete, the batch is cooled to approximately 25° C. The crude reaction mixture is absorbed onto silica (~500 g) and eluted over silica (1.5 kg) with 10% ethyl acetate in heptane to obtain the product as a solid (132.9 g, 87.3%). The product is crystallized from heptane (23 L/kg) and isopropanol (0.4 L/kg) to yield the title compound (119.5 g; 78.5% yield) as an off-white solid. MS (ES): 265.21 [M−1]$^-$. $^1$H NMR (400 MHz, CDCl$_3$): δ 7.68 (d, 2H), 7.26 (d, 2H), 6.62 (s, 2H), 4.73 (s, 1H), 1.97 (s, 6H).

Preparation 2

4'-tert-butyl-2,6-dimethylbiphenyl-4-ol

Prepare the title compound by essentially following the procedure as described in Preparation 1, using 4-tert-butylphenylboronic acid. $^1$H NMR (400 MHz, CDCl$_3$): δ 7.43 (d, 2H), 7.06 (d, 2H), 6.61 (s, 2H), 4.85 (s, 1H), 2.02 (s, 6H), 1.38 (s, 9H).

Preparation 3

(R,S)-5-(1-Hydroxy-3-methyl-butyl)-thiophene-2-carboxylic acid ethyl ester

A solution of diisopropylamine (8.55 mL, 60 mmol) in THF (350 mL) under N$_2$ is cooled to −78° C. and treated with n-butyllithium (2.5 M in hexanes, 24 mL). The mixture is then warmed to 0° C. for 10 min, cooled back to −78° C., treated dropwise with a solution of thiophene-2-carboxylic acid ethyl ester (7.8 g, 50 mmol) in THF (150 mL), and stirred 5 min. 3-Methyl-butyraldehyde (6.48 mL, 60 mmol) is then added, and the reaction is allowed to warm to room temperature, while stirring overnight. Aqueous buffer (pH=7) is added, and the product is extracted into ethyl acetate (3×). Combined organic layers are dried, filtered, and concentrated. The resulting residue is applied to silica gel and eluted using hexanes with an ethyl acetate gradient from 0% to 60% to give the title compound (8.03 g).

Preparations 4 to 9 are prepared in a substantially similar manner as described in Preparation 3.

Preparation 4

(R,S)-5-(1-Hydroxy-propyl)-thiophene-2-carboxylic acid ethyl ester

Preparation 5

(R,S)-5-(1-Hydroxy-butyl)-thiophene-2-carboxylic acid ethyl ester

Preparation 6

(R,S)-5-(1-Hydroxy-pentyl)-thiophene-2-carboxylic acid ethyl ester

Preparation 7

(R,S)-5-(1-Hydroxy-2,2-dimethyl-propyl)-thiophene-2-carboxylic acid ethyl ester

Preparation 8

(R,S)-5-(1-Hydroxy-2-methyl-propyl)-thiophene-2-carboxylic acid ethyl ester

Preparation 9

(R,S)-5-(1-Hydroxy-3,3-dimethyl-butyl)-thiophene-2-carboxylic acid ethyl ester

Preparation 10

4'-tert-Butyl-2,6-dimethyl-biphenyl-4-thiol

Step A. Dimethyl-thiocarbamic acid O-(4'-tert-butyl-2,6-dimethyl-biphenyl-4-yl) ester To a solution of 4'-tert-butyl-2,6-dimethyl-biphenyl-4-ol (10 g, 37.3 mmol) in dioxane (157 mL) is added 4-dimethylaminopyridine (476 mg, 3.9 mmol), triethylamine (10 mL, 78.6 mmol), and dimethylthiocarbamoyl chloride (6.1 g, 49.1 mmol). The reaction mixture is heated to reflux overnight. After cooling to room temperature, the reaction mixture is partitioned between ethyl acetate and water. The aqueous layer is back-extracted with ethyl acetate, and the combined organic layers are dried and concentrated. The resulting residue is applied to silica gel and eluted using 20% ethyl acetate in hexanes to give dimethyl-thiocarbamic acid O-(4'-tert-butyl-2,6-dimethyl-biphenyl-4-yl) ester (12.2 g).

Step B. Dimethyl-thiocarbamic acid S-(4'-tert-butyl-2,6-dimethyl-biphenyl-4-yl) ester A suspension of dimethyl-thiocarbamic acid O-(4'-tert-butyl-2,6-dimethyl-biphenyl-4-yl) ester (12.1 g, 35.4 mmol) in tetradecane (80 mL) is heated at 245° C. for 16 h. After cooling to room temperature, a solid precipitate is filtered, washed with heptane, and dried under vacuum at 40° C. The resulting residue is applied to silica gel and eluted using hexanes with an ethyl acetate gradient from 0% to 60% to give dimethyl-thiocarbamic acid S-(4'-tert-butyl-2,6-dimethyl-biphenyl-4-yl) ester (8.86 g).

Step C. 4'-tert-Butyl-2,6-dimethyl-biphenyl-4-thiol

To a solution of dimethyl-thiocarbamic acid S-(4'-tert-butyl-2,6-dimethyl-biphenyl-4-yl) ester (8.8 g, 25.8 mmol) in methanol (65 mL) is added sodium methoxide (1.39 g, 25.8 mmol). The reaction mixture is heated to reflux overnight. After cooling to room temperature, the reaction mixture is neutralized with 5N HCl, concentrated to ⅓ volume, treated with brine, and extracted into dichloromethane. The aqueous layer is back-extracted with dichloromethane, and the combined organic layers are dried and concentrated. The resulting residue is applied to silica gel and eluted using hexanes with an ethyl acetate gradient from 0% to 50% to give the title compound (5.84 g).

Preparation 11

2,6-Dimethyl-4'-trifluoromethyl-biphenyl-4-thiol

The titled compound is prepared in a substantially similar manner as described in Preparation 10 using 2,6-dimethyl-4'-(trifluoromethyl)biphenyl-4-ol. MS (ES): 281.1 [M–H]⁻.

Example 1

(R,S)-5-[1-(4'-tert-Butyl-2,6-dimethyl-biphenyl-4-ylsulfanyl)-2-methyl-propyl]-thiophene-2-carboxylic acid (2H-tetrazol-5-ylmethyl)-amide

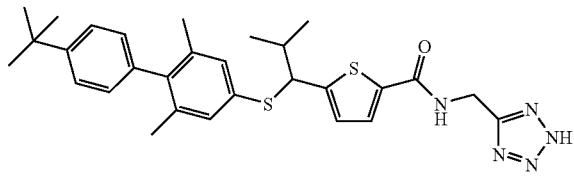

Step A. (R,S)-5-[1-(4'-tert-Butyl-2,6-dimethyl-biphenyl-4-ylsulfanyl)-2-methyl-propyl]-thiophene-2-carboxylic acid ethyl ester A solution of (R,S)-5-(1-hydroxy-2-methyl-propyl)-thiophene-2-carboxylic acid ethyl ester (1.26 g, 5.52 mmol) and 4'-tert-butyl-2,6-dimethyl-biphenyl-4-thiol (1.64 g, 6.07 mmol) in 1,2-dichloroethane (22 mL) is treated with zinc iodide (1.76 g, 5.52 mmol) and stirred overnight at room temperature. The reaction mixture is then partitioned between water and dichloromethane. The aqueous layer is back-extracted with dichloromethane, and the combined organic layers are dried, filtered, and concentrated. The resulting residue is applied to silica gel and eluted using hexanes with an ethyl acetate gradient from 0% to 40% to give (R,S)-5-[1-(4'-tert-butyl-2,6-dimethyl-biphenyl-4-ylsulfanyl)-2-methyl-propyl]-thiophene-2-carboxylic acid ethyl ester (2.08 g). MS (ES): 481.1 [M+H]⁺.

Step B. (R,S)-5-[1-(4'-tert-butyl-2,6-dimethyl-biphenyl-4-ylsulfanyl)-2-methyl-propyl]-thiophene-2-carboxylic acid To a mixture of (R,S)-5-[1-(4'-tert-butyl-2,6-dimethyl-biphenyl-4-ylsulfanyl)-2-methyl-propyl]-thiophene-2-carboxylic acid ethyl ester (2.08 g, 4.33 mmol) in ethanol (43 mL) is added sodium hydroxide (5N aqueous, 4.33 mL) at room temperature, and stirred overnight. The reaction mixture is acidified by 1N HCl (4.42 mL), extracted into ethyl acetate, dried and concentrated, then dried under vacuum, giving (R,S)-5-[1-(4'-tert-butyl-2,6-dimethyl-biphenyl-4-ylsulfanyl)-2-methyl-propyl]-thiophene-2-carboxylic acid (1.82 g). MS (ES): 451.2 [M–H]⁻.

Step C. (R,S)-5-[1-(4'-tert-Butyl-2,6-dimethyl-biphenyl-4-ylsulfanyl)-2-methyl-propyl]-thiophene-2-carboxylic acid cyanomethyl-amide To a mixture of (R,S)-5-[1-(4'-tert-butyl-2,6-dimethyl-biphenyl-4-ylsulfanyl)-2-methyl-propyl]-thiophene-2-carboxylic acid (342 mg, 0.756 mmol) in DMF (7.6 mL) is added N-(3-dimethylaminopropyl)-N'-ethylcarbodiimide hydrochloride (290 mg, 1.512 mmol), 1-hydroxybenzotriazole hydrate (123 mg, 0.907 mmol), and diisopropylethylamine (0.264 mL, 1.512 mmol) at room temperature, and stirred 10 min. The mixture is then treated with aminoacetonitrile hydrochloride (84 mg, 0.907 mmol), and stirred overnight. The reaction mixture is treated with 0.1N HCl and extracted into ethyl acetate twice. The combined organic layers are washed with brine, dried and concentrated, and the resulting residue is applied to silica gel and eluted using hexanes with an ethyl acetate gradient from 0% to 70% to give (R,S)-5-[1-(4'-tert-butyl-2,6-dimethyl-biphenyl-4-ylsulfanyl)-2-methyl-propyl]-thiophene-2-carboxylic acid cyanomethyl-amide (289 mg). MS (ES): 491.1 [M+H]⁺.

Step D. (R,S)-5-[1-(4'-tert-Butyl-2,6-dimethyl-biphenyl-4-ylsulfanyl)-2-methyl-propyl]-thiophene-2-carboxylic acid (2H-tetrazol-5-ylmethyl)-amide A solution of (R,S)-5-[1-(4'-tert-butyl-2,6-dimethyl-biphenyl-4-ylsulfanyl)-2-methyl-propyl]-thiophene-2-carboxylic acid cyanomethyl-amide (195 mg, 0.397 mmol) in toluene (8 mL) is treated with triethylamine hydrochloride (275 mg, 2 mmol) and sodium azide (130 mg, 2 mmol), then heated at reflux overnight (thermal conditions) or alternatively, placed in a CEM microwave reactor for 20 min. (300 W, 180° C., $N_2$ cooling) (microwave conditions). After cooling to room temperature, the reaction mixture is partitioned between ethyl acetate and water. The aqueous layer is back-extracted with ethyl acetate, the combined organic layers are dried and concentrated, and the resulting residue is loaded onto $C_{18}$ and eluted using water with an acetonitrile gradient from 15% to 100% to give the title compound (91 mg). MS (ES): 534.2 [M+H]⁺.

Examples 2 to 7 are prepared in a substantially similar manner using the thermal conditions as described in Example 1, Step D.

Example 2

(±)-5-[1-(4'-tert-Butyl-2,6-dimethyl-biphenyl-4-ylsulfanyl)-propyl]-thiophene-2-carboxylic acid (2H-tetrazol-5-ylmethyl)-amide

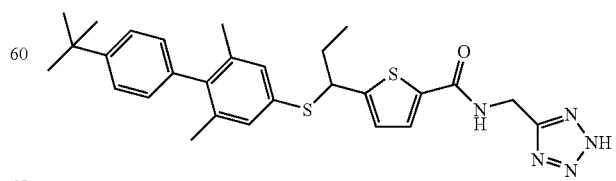

MS (ES): 520.3 [M+H]⁺.

Example 3

(±)-5-[1-(4'-tert-Butyl-2,6-dimethyl-biphenyl-4-yl-sulfanyl)-butyl]-thiophene-2-carboxylic acid (2H-tetrazol-5-ylmethyl)-amide

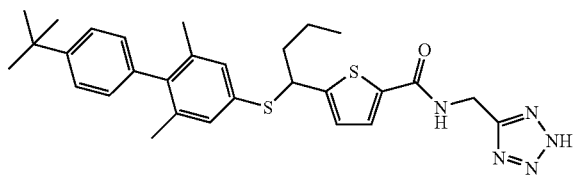

MS (ES): 534.3 $[M+H]^+$.

Example 4

(±)-5-[1-(4'-tert-Butyl-2,6-dimethyl-biphenyl-4-yl-sulfanyl)-pentyl]-thiophene-2-carboxylic acid (2H-tetrazol-5-ylmethyl)-amide

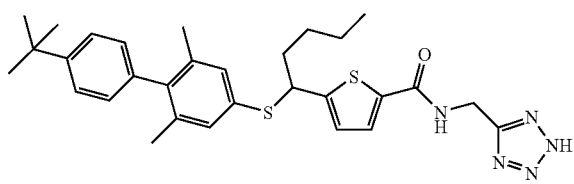

MS (ES): 548.3 $[M+H]^+$.

Example 5

(±)-5-[1-(4'-tert-Butyl-2,6-dimethyl-biphenyl-4-yl-sulfanyl)-3-methyl-butyl]-thiophene-2-carboxylic acid (2H-tetrazol-5-ylmethyl)-amide

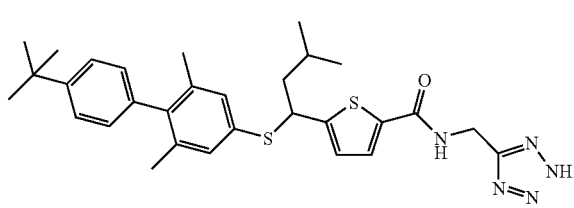

MS (ES): 548.0 $[M+H]^+$.

Example 6

((±)-5-[1-(4'-tert-Butyl-2,6-dimethyl-biphenyl-4-ylsulfanyl)-3,3-dimethyl-butyl]-thiophene-2-carboxylic acid (2H-tetrazol-5-ylmethyl)-amide

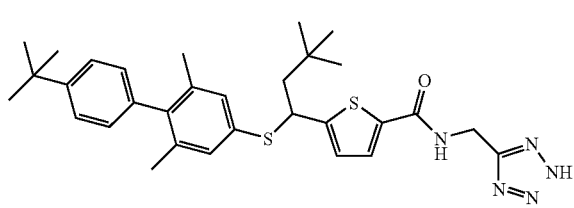

MS (ES): 562.0 $[M+H]^+$.

Example 7

(±)-5-[1-(4'-tert-Butyl-2,6-dimethyl-biphenyl-4-yl-sulfanyl)-2,2-dimethyl-propyl]-thiophene-2-carboxylic acid (2H-tetrazol-5-ylmethyl)-amide

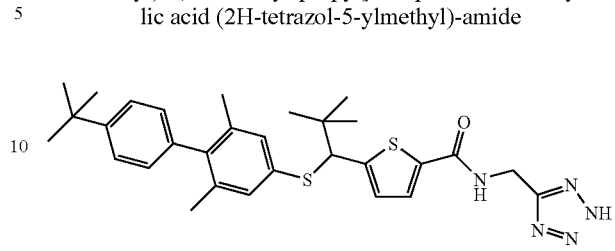

MS (ES): 548.3 $[M+H]^+$.

Examples 8 to 13 are prepared in a substantially similar manner using the microwave conditions as described in Example 1, Step D.

Example 8

(±)-5-[1-(2,6-Dimethyl-4'-trifluoromethyl-biphenyl-4-ylsulfanyl)-butyl]-thiophene-2-carboxylic acid (1H-tetrazol-5-ylmethyl)-amide

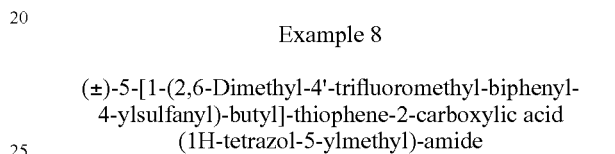

MS (ES): 546.0 $[M+H]^+$.

Example 9

(±)-5-[1-(2,6-Dimethyl-4'-trifluoromethyl-biphenyl-4-ylsulfanyl)-2-methyl-propyl]-thiophene-2-carboxylic acid (1H-tetrazol-5-ylmethyl)-amide

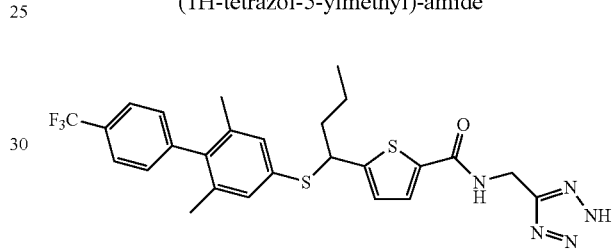

MS (ES): 545.8 $[M+H]^+$.

Example 10

(±)-5-[1-(2,6-Dimethyl-4'-trifluoromethyl-biphenyl-4-ylsulfanyl)-2,2-dimethyl-propyl]-thiophene-2-carboxylic acid (1H-tetrazol-5-ylmethyl)-amide

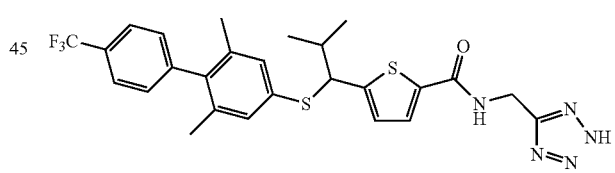

MS (ES): 560.0 $[M+H]^+$.

Example 11

(±)-5-[1-(2,6-Dimethyl-4'-trifluoromethyl-biphenyl-4-ylsulfanyl)-3-methyl-butyl]-thiophene-2-carboxylic acid (1H-tetrazol-5-ylmethyl)-amide

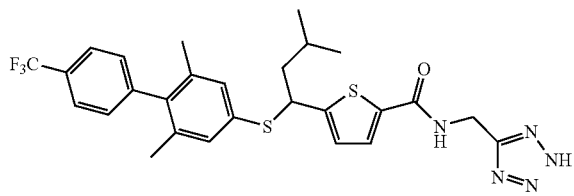

MS (ES): 560.0 [M+H]$^+$.

Example 12

(±)-5-[1-(2,6-Dimethyl-4'-trifluoromethyl-biphenyl-4-ylsulfanyl)-3,3-dimethyl-butyl]-thiophene-2-carboxylic acid (1H-tetrazol-5-ylmethyl)-amide

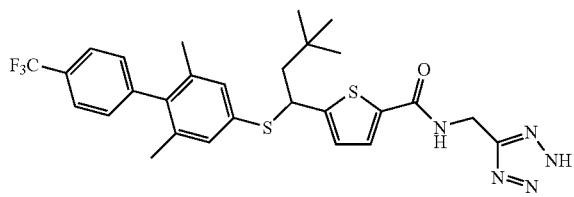

MS (ES): 574.0 [M+H]$^+$.

Example 13

(±)-5-[1-(2,6-Dimethyl-4'-trifluoromethyl-biphenyl-4-ylsulfanyl)-pentyl]-thiophene-2-carboxylic acid (1H-tetrazol-5-ylmethyl)-amide

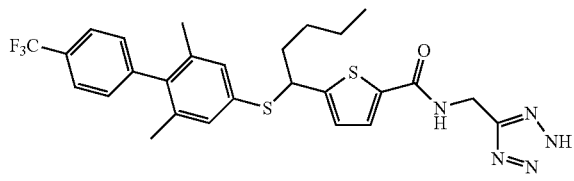

MS (ES): 560.0 [M+H]$^+$.

Example 14

5-[1-(4'-tert-Butyl-2,6-dimethyl-biphenyl-4-ylsulfanyl)-2,2-dimethyl-propyl]-thiophene-2-carboxylic acid (2H-tetrazol-5-ylmethyl)-amide (Isomer 1)

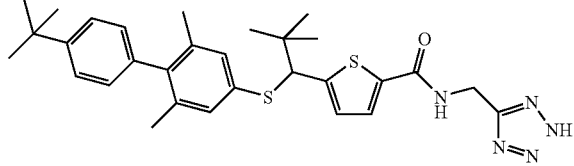

Step A. 5-[1-(4'-tert-Butyl-2,6-dimethyl-biphenyl-4-ylsulfanyl)-2,2-dimethyl-propyl]-thiophene-2-carboxylic acid cyanomethyl-amide (Isomer 1)

(±)-5-[1-(4'-tert-Butyl-2,6-dimethyl-biphenyl-4-ylsulfanyl)-2,2-dimethyl-propyl]-thiophene-2-carboxylic acid cyanomethyl-amide (500 mg) is separated by chiral HPLC (column: Chiralpak AD 4.6×150 mm; eluent: 15/85 3A ethanol/heptane, with 12% dimethylethylamine; flow rate: 0.6 mL/min; UV absorbance wavelength: 300 nm) to provide 5-[1-(4'-tert-Butyl-2,6-dimethyl-biphenyl-4-ylsulfanyl)-2,2-dimethyl-propyl]-thiophene-2-carboxylic acid cyanomethyl-amide (Isomer 1) (220 mg).

Step B. 5-[1-(4'-tert-Butyl-2,6-dimethyl-biphenyl-4-ylsulfanyl)-2,2-dimethyl-propyl]-thiophene-2-carboxylic acid (2H-tetrazol-5-ylmethyl)-amide (Isomer 1)

A solution of 5-[1-(4'-tert-Butyl-2,6-dimethyl-biphenyl-4-ylsulfanyl)-2,2-dimethyl-propyl]-thiophene-2-carboxylic acid cyanomethyl-amide (Isomer 1) (220 mg, 0.436 mmol) in toluene (8.7 mL) is treated with triethylamine hydrochloride (300 mg, 2.18 mmol) and sodium azide (142 mg, 2.18 mmol), then heated at reflux overnight (thermal conditions) or alternatively, placed in a CEM microwave reactor for 20 min (300 W, 180° C., N$_2$ cooling) (microwave conditions). After cooling to room temperature, the reaction mixture is partitioned between ethyl acetate and water. The aqueous layer is back-extracted with ethyl acetate, and the combined organic layers are dried and concentrated to give the title compound (105 mg). MS (ES): 548.3 [M+H]$^+$.

Example 15 to 17 are prepared in a substantially similar manner using the thermal conditions as describe in Example 14, Step B.

Example 15

5-[1-(4'-tert-Butyl-2,6-dimethyl-biphenyl-4-ylsulfanyl)-2,2-dimethyl-propyl]-thiophene-2-carboxylic acid (2H-tetrazol-5-ylmethyl)-amide (Isomer 2)

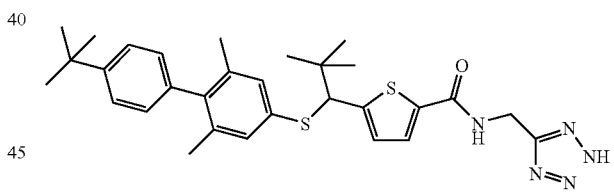

MS (ES): 548.3 [M+H]$^+$.

Example 16

5-[1-(4'-tert-Butyl-2,6-dimethyl-biphenyl-4-ylsulfanyl)-propyl]-thiophene-2-carboxylic acid (2H-tetrazol-5-ylmethyl)-amide (Isomer 1)

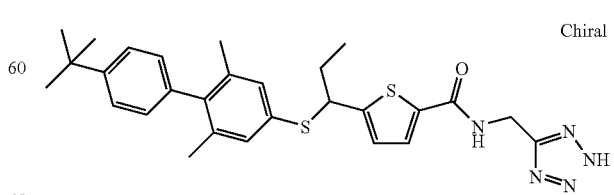

MS (ES): 519.8 [M+H]$^+$.

Example 17

5-[1-(4'-tert-Butyl-2,6-dimethyl-biphenyl-4-ylsulfanyl)-propyl]-thiophene-2-carboxylic acid (2H-tetrazol-5-ylmethyl)-amide (Isomer 2)

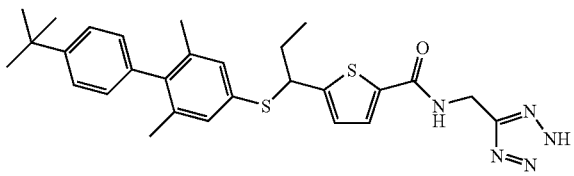

MS (ES): 520.3 [M+H]$^+$.

Examples 18 to 29 are prepared in a substantially similar manner using the microwave conditions as described in Example 14, Step B.

Example 18

5-[1-(2,6-Dimethyl-4'-trifluoromethyl-biphenyl-4-ylsulfanyl)-butyl]-thiophene-2-carboxylic acid (1H-tetrazol-5-ylmethyl)-amide (Isomer 1)

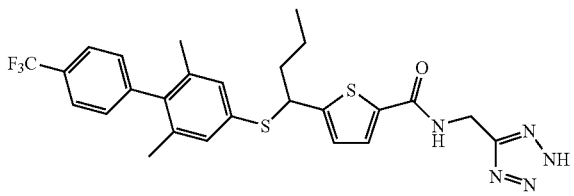

MS (ES): 546.0 [M+H]$^+$.

Example 19

5-[1-(2,6-Dimethyl-4'-trifluoromethyl-biphenyl-4-ylsulfanyl)-butyl]-thiophene-2-carboxylic acid (1H-tetrazol-5-ylmethyl)-amide (Isomer 2)

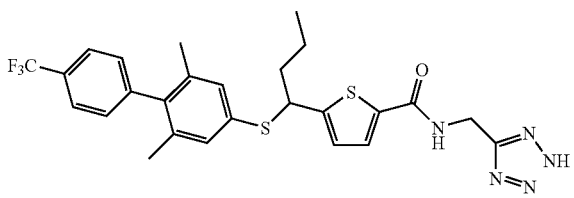

MS (ES): 546.0 [M+H]$^+$.

Example 20

5-[1-(2,6-Dimethyl-4'-trifluoromethyl-biphenyl-4-ylsulfanyl)-2-methyl-propyl]-thiophene-2-carboxylic acid (1H-tetrazol-5-ylmethyl)-amide (Isomer 1)

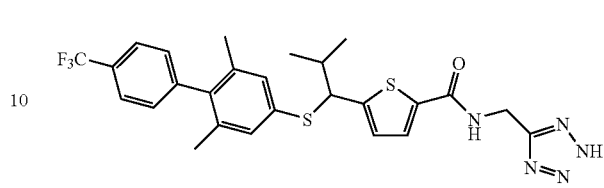

MS (ES): 546.0 [M+H]$^+$.

Example 21

5-[1-(2,6-Dimethyl-4'-trifluoromethyl-biphenyl-4-ylsulfanyl)-2-methyl-propyl]-thiophene-2-carboxylic acid (1H-tetrazol-5-ylmethyl)-amide (Isomer 2)

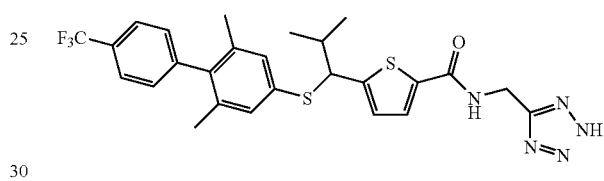

MS (ES): 546.0 [M+H]$^+$.

Example 22

5-[1-(2,6-Dimethyl-4'-trifluoromethyl-biphenyl-4-ylsulfanyl)-2,2-dimethyl-propyl]-thiophene-2-carboxylic acid (1H-tetrazol-5-ylmethyl)-amideb (Isomer 1)

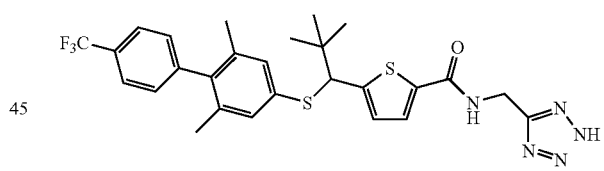

MS (ES): 559.8 [M+H]$^+$.

Example 23

5-[1-(2,6-Dimethyl-4'-trifluoromethyl-biphenyl-4-ylsulfanyl)-2,2-dimethyl-propyl]-thiophene-2-carboxylic acid (1H-tetrazol-5-ylmethyl)-amideb (Isomer 2)

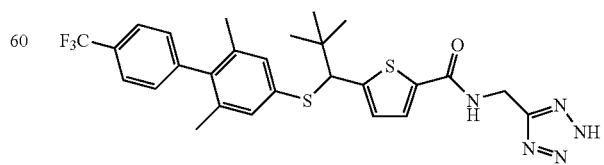

MS (ES): 559.8 [M+H]$^+$.

Example 24

5-[1-(2,6-Dimethyl-4'-trifluoromethyl-biphenyl-4-ylsulfanyl)-3-methyl-butyl]-thiophene-2-carboxylic acid (1H-tetrazol-5-ylmethyl)-amide (Isomer 1)

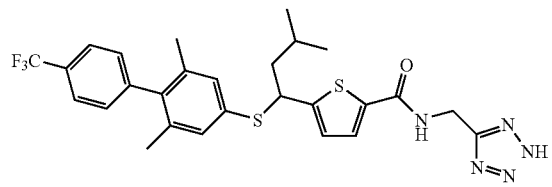

MS (ES): 560.0 [M+H]$^+$.

Example 25

5-[1-(2,6-Dimethyl-4'-trifluoromethyl-biphenyl-4-ylsulfanyl)-3-methyl-butyl]-thiophene-2-carboxylic acid (1H-tetrazol-5-ylmethyl)-amide (Isomer 2)

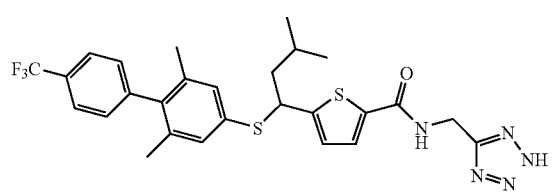

MS (ES): 560.0 [M+H]$^+$.

Example 26

5-[1-(2,6-Dimethyl-4'-trifluoromethyl-biphenyl-4-ylsulfanyl)-3,3-dimethyl-butyl]-thiophene-2-carboxylic acid (1H-tetrazol-5-ylmethyl)-amide (Isomer 1)

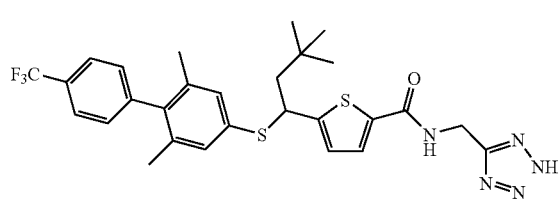

MS (ES): 573.8 [M+H]$^+$.

Example 27

5-[1-(2,6-Dimethyl-4'-trifluoromethyl-biphenyl-4-ylsulfanyl)-3,3-dimethyl-butyl]-thiophene-2-carboxylic acid (1H-tetrazol-5-ylmethyl)-amide (Isomer 2)

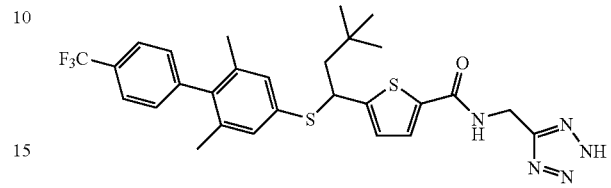

MS (ES): 573.8 [M+H]$^+$.

Example 28

5-[1-(2,6-Dimethyl-4'-trifluoromethyl-biphenyl-4-ylsulfanyl)-pentyl]-thiophene-2-carboxylic acid (1H-tetrazol-5-ylmethyl)-amide (Isomer 1)

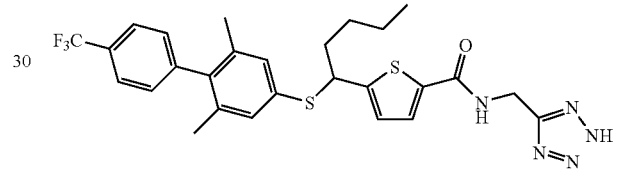

MS (ES): 559.8 [M+H]$^+$.

Example 29

5-[1-(2,6-Dimethyl-4'-trifluoromethyl-biphenyl-4-ylsulfanyl)-pentyl]-thiophene-2-carboxylic acid (1H-tetrazol-5-ylmethyl)-amide (Isomer 2)

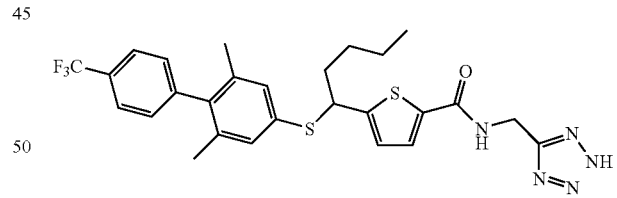

MS (ES): 559.8 [M+H]$^+$.

The compound of Formula I is preferably formulated in a unit dosage form prior to administration. Therefore, yet another embodiment of the present invention is a pharmaceutical composition comprising a compound of Formula I and one or more pharmaceutically acceptable carriers, diluents or excipients. In such form, the preparation is subdivided into suitably sized unit doses containing appropriate quantities of the active components, e.g., an effective amount to achieve the desired purpose. Such pharmaceutical compositions and processes for preparing same are well known in the art. See, e.g., REMINGTON: THE SCIENCE AND PRACTICE OF PHARMACY (A. Gennaro, et al., eds., 19$^{th}$ ed., Mack Publishing Co., 1995). The particular dosage of a compound of formula (1) or a pharmaceutically acceptable salt thereof required to constitute an effective amount according to this invention will depend upon the particular circumstances of the conditions to be treated. Preferably the compound is administered orally. The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day. Considerations such as dosage, route of administration, and frequency of dosing are best decided by the attending physician.

The compositions of the invention may be formulated so as to provide quick, sustained or delayed release of the active ingredient after administration to the patient. The compositions of the present invention may be formulated in sustained release form to provide the rate controlled release of any one or more of the components or active ingredients to optimize the therapeutic effects, i.e., glucagon receptor antagonist activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

There is increasing evidence that glucagon plays an important role in glucose homeostasis. Compounds of Formula I are effective as antagonists or inverse agonists of the glucagon receptor, and thus inhibit the activity of the glucagon receptor. More particularly, these compounds are selective antagonists or inverse agonists of the glucagon receptor. As selective antagonists or inverse agonists, the compounds of Formula I are useful in the treatment of diseases, disorders, or conditions responsive to the inactivation of the glucagon receptor, including but not limited to diabetic and other glucagon related disorders. It is expected that selective antagonists or inverse agonists of the glucagon receptor will lower plasma glucose levels and thus prevent or treat diabetic and other glucagon related metabolic disorders.

Pharmacological Methods

In the following section binding assays as well as functional assays useful for evaluating the efficiency of the compounds of the invention are described. Binding of compounds to the glucagon receptor may be determined in a competition binding assay using the cloned human glucagon receptor, and selectivity against the hGlp1 receptor. Antagonism may be determined as the ability of the compounds to inhibit the amount of cAMP formed in the assay in the presence of 5 nM glucagon.

Glucagon Receptor (hGlucR) Binding Assay

The receptor binding assay uses cloned human glucagon receptor (Lok S, Kuijper J L, Jelinek L J, Kramer J M, Whitmore T E, Sprecher C A, Mathewes S, Grant F J, Biggs S H, Rosenberg G B, et al. Gene 140 (2), 203-209 (1994)) isolated from 293HEK membranes. The hGlucR cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA is transfected into 293 HEK cells and selected with 200 µg/mL Hygromycin.

Crude plasma membranes are prepared using cells from suspension culture. The cells are lysed on ice in hypotonic buffer containing 25 mM Tris HCL, pH 7.5, 1 mM MgCl2, DNAse1, 20 u/mL, and Roche Complete Inhibitors-without EDTA. The cell suspension is homogenized with a glass dounce homogenizer using a Teflon pestle for 25 strokes. The homogenate is centrifuged at 4 degrees C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4 degrees C. The membrane pellet is resuspended in homogenization buffer and stored as frozen aliquots at −80 degree C. freezer until needed.

Glucagon is radioiodinated by I-125-lactoperoxidase procedure and purified by reversed phase HPLC at Perkin-Elmer/NEN (NEX207). The specific activity is 2200 Ci/mmol. Kd determination is performed by homologous competition instead of saturation binding due to high propanol content in the I-125 glucagon material. The Kd is estimated to be 3 nM and is used to calculate Ki values for all compounds tested.

The binding assays are carried out using a Scintillation Proximity Assay (Amersham) with WGA beads previously blocked with 1% fatty acid free BSA (ICN). The binding buffer contains 25 mM Hepes, pH 7.4, 2.5 mM $CaCl_2$, 1 mM $MgCl_2$, 0.1% fatty acid free BSA, (ICN), 0.003% tween-20, and Roche Complete Inhibitors without EDTA. Glucagon is dissolved in 0.01 N HCl at 1 mg/mL and immediately frozen at −80 degrees C. in 30 µl aliquots. The glucagon aliquot is diluted and used in binding assays within an hour. Test compounds are dissolved in DMSO and serially diluted in DMSO. 10 ul diluted compounds or DMSO is transferred into Corning 3632, opaque clear bottom assay plates containing 90 µl assay binding buffer or cold glucagon (NSB at 1 µM final). 50 µl of 1-125 glucagon (0.15 nM final in reaction), 50 µl of membranes (300 µg/well), and 40 µl of WGA beads (150 mgs/well) are added, covered, and mixed end over end. Plates are read with a MicroBeta after 14 hours of settling time at room temp.

Results are calculated as a percent of specific I-125-glucagon binding in the presence of compound. The absolute EC50 dose of compound is derived by non-linear regression of percent specific binding of I-125-glucagon vs. the dose of compound added. The EC50 dose is converted to Ki using the Cheng-Prusoff equation (Cheng Y., Prusoff W. H., Biochem. Pharmacol. 22, 3099-3108, 1973).

Glucagon-Like-Peptide 1 (Glp1-R) Receptor Binding Assay

The receptor binding assay uses cloned human glucagon-like peptide 1 receptor (hGlp1-R) (Graziano M P, Hey P J, Borkowski D, Chicchi G G, Strader C D, Biochem Biophys Res Commun. 1993 Oct. 15; 196(1):141-6) isolated from 293HEK membranes. The hGlp1-R cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA is transfected into 293 HEK cells and selected with 200 μg/mL Hygromycin.

Crude plasma membrane is prepared using cells from suspension culture. The cells are lysed on ice in hypotonic buffer containing 25 mM Tris HCl, pH 7.5, 1 mM $MgCl_2$, DNAse, 20 W/mL, and Roche Complete Inhibitors without EDTA. The cell suspension is homogenized with a glass dounce homogenizer using a Teflon pestle for 25 strokes. The homogenate is centrifuged at 4 degrees C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4 degrees C. The membrane pellet is resuspended in homogenization buffer and stored as frozen aliquots in −80 degree C. freezer until use.

Glucagaon-like peptide 1 (Glp-1) is radioiodinated by the I-125-lactoperoxidase procedure and purified by reversed phase HPLC at Perkin-Elmer/NEN (NEX308). The specific activity is 2200 Ci/mmol. Kd determination is performed by homologous competition instead of saturation binding due to high propanol content in the 1-125 Glp-1 material. The Kd is estimated to be 3 nM and is used to calculate Ki values for all compounds tested.

The binding assays are carried out using a Scintillation Proximity Assay (Amersham) with wheat germ agglutinin (WGA) beads previously blocked with 1% fatty acid free BSA (ICN). The binding buffer contains 25 mM Hepes, pH 7.4, 2.5 mM $CaCl_2$, 1 mM $MgCl_2$, 0.1% fatty acid free BSA, (ICN), 0.003% tween-20, and Roche Complete Inhibitors without EDTA. Glucagon-like peptide 1 is dissolved in PBS at 1 mg/mL and immediately frozen at −80 degrees C. in 30 ul aliquots. The glucagon-like peptide aliquot is diluted and used in binding assays within an hour. Test compounds are dissolved in DMSO and serially diluted in DMSO. 10 μl diluted compounds or DMSO is transferred into Corning 3632, opaque clear bottom assay plates containing 90 μl assay binding buffer or cold glucagon-like peptide 1 (NSB at 1 μM final). 50 μl of 1-125 glucagon-like peptide 1 (0.15 nM final in reaction), 50 μl of membranes (600 μg/well), and 40 μl of WGA beads (150 μgs/well) are added, covered, and mixed end over end. Plates are read with a MicroBeta after 14 hours of settling time at room temp.

Results are calculated as a percent of specific I-125-glucagon-like peptide 1 binding in the presence of compound. The absolute EC50 dose of compound is derived by non-linear regression of percent specific binding of I-125-glucagon-like peptide 1 vs. the dose of compound added. The EC50 dose is converted to Ki using the Cheng-Prusoff equation (Cheng Y., Prusoff W. H., Biochem. Pharmacol. 22, 3099-3108, 1973).

Glucagon-Stimulated cAMP Functional Antagonist Assay

The cAMP functional assay uses the same cloned human glucagon receptor cell line isolated for the hGlucR binding assay described above. Cells are stimulated with a mixture of an EC80 dose of glucagon in the presence of compound. The cAMP generated within the cell is quantitated using an Amplified Luminescent Proximity Homogeneous Assay, Alpha Screen, from Perkin Elmer (6760625R).

Briefly, cAMP within the cell competes for binding of biotinylated cAMP from the kit to a coated anti-cAMP antibody Acceptor bead and a strepavidin coated Donor bead. As the cAMP level within the cell increases, a disruption of the Acceptor bead-biotinlyated cAMP—Donor bead complex occurs and decreases the signal.

Glucagon is dissolved in 0.01 N HCl at 1 mg/mL and immediately frozen at −80 degrees C. in 30 ul aliquots. The glucagon aliquot is diluted and used in the functional assay within an hour. Cells are harvested from sub-confluent tissue culture dishes with Enzyme-Free Cell Dissociation Solution, (Specialty Media 5-004-B). The cells are pelleted at low speed and washed 3 times with assay buffer [25 mM Hepes in HBSS-with Mg and Ca (GIBCO, 14025-092) with 0.1% Fatty Acid Free BSA (ICN)] then diluted to a final concentration of 250,000 cells per mL. Compounds are serially diluted into DMSO then diluted into assay buffer with a 3× concentration of glucagon and 3% DMSO. The EC80 of glucagon is pre-determined from a full glucagon dose response and represents the dose at which glucagons produces an 80% of the maximal glucagon response. A mixture of biotinylated cAMP (1 unit/well final) from the Alpha Screen Kit and 3×IBMX (1500 μM) is prepared in Assay Buffer.

The functional assay is performed in 96 well, low-volume, white, poylstyrene Costar Plates (3688). The biotinylated cAMP/IBMX mixture, 0.02 mLs, is placed into each well, followed by addition of 0.02 mLs of glucagon dose response, cAMP standard curve, or compound/glucagon mixtures. The reaction is started by addition of 0.02 mLs of cells (5000/well final). After 60 minutes at room temperature, the reaction is stopped by the addition of 0.03 mLs of Lysis Buffer [10 mM Hepes, pH 7.4, 1% NP40, and 0.01% fatty acid free BSA (ICN) containing 1 unit each/well of Acceptor and Donor beads from the Alpha Screen Kit]. Lysis Buffer addition is performed under a green light to prevent bleaching of the detection beads. The plates are wrapped in foil and left to equilibrate overnight at room temperature. The plates are read on a Packard Fusion™-α Instrument.

Alpha screen units are converted to pmoles cAMP generated per well based upon the cAMP standard curve. The pmoles cAMP produced in the presence of compound are converted to % of a maximal response with the EC80 dose of glucagon alone. With each experiment, the dose of glucagon needed to produce a 50% response of pmoles cAMP is determined. This EC50 dose is used to normalize results to a Kb using a modified Cheng-Prusoff equation (Cheng Y., Prusoff W. H., Biochem. Pharmacol. 22, 3099-3108, 1973), where Kb=(EC50 compound)/[1+(pM glucagon used/EC50 in pM for glucagon dose response)].

The compounds according to the invention preferably have a Ki value of no greater than 50 μM as determined by the Glucagon Receptor (hGlucR) Binding Assay disclosed herein. More preferably, the compounds according to the invention have a Ki value of less than 5 μM, preferably of less than 500 nM and even more preferred of less than 100 nM as determined by the Glucagon Receptor (hGlucR) Binding Assay disclosed herein. Generally, the compounds according to the invention show a higher affinity for the glucagon receptor compared to the GLP-1 receptor, and preferably have a higher binding affinity to the glucagon receptor than to the GLP-1 receptor. All of the examples provided herein have a Ki value of less than 10 μM.

The results are given below for the indicated compound.

TABLE 1

| Example | Ki (nM) |
|---|---|
| 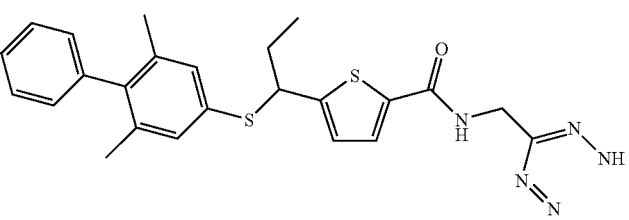<br>Example 17 | 18.4 |
| 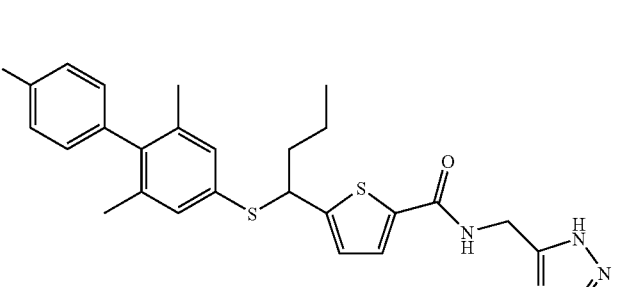<br>Example 18 | 36.0 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed:

1. A compound structurally represented by Formula I

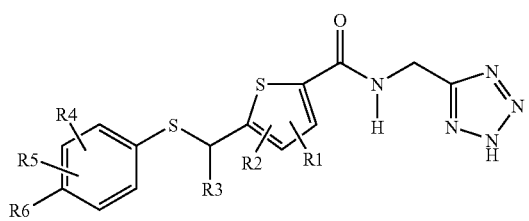

(I)

or a pharmaceutically acceptable salt thereof wherein:

R1 and R2 are independently —H or -halogen;

R3 is
- —($C_1$-$C_8$)alkyl (optionally substituted with 1 to 3 halogens), —($C_3$-$C_7$)cycloalkyl,
- —($C_1$-$C_6$)alkyl-($C_3$-$C_7$)cycloalkyl, or —($C_3$-$C_7$)cycloalkyl-($C_1$-$C_6$)alkyl (optionally substituted with 1 to 3 halogens);

R4 and R5 are independently
- —H, -halogen, -hydroxy, hydroxymethyl, —CN, —($C_1$-$C_7$)alkoxy, —($C_2$-$C_7$)alkenyl, or
- —($C_1$-$C_6$)alkyl (optionally substituted with 1 to 3 halogens);

R6 is

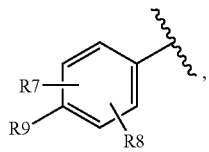

wherein the zig-zag mark shows the point of attachment to the parent molecule;

R7 and R8 are independently
- —H, -halogen, —($C_1$-$C_6$)allyl (optionally substituted with 1 to 3 halogens),
- —($C_1$-$C_6$)alkoxy, —($C_3$-$C_7$)cycloalkyl, —C(O)R10, —COOR10, —OC(O)R10,
- —OS(O)$_2$R10, —SR10, —S(O)R10, —S(O)$_2$R10, or —O($C_2$-$C_7$)alkenyl;

R9 is independently
- —H, -halogen, —CN, —($C_3$-$C_7$)cycloalkyl, —C(O)R10, —COOR10, —OC(O)R10,
- —OS(O)$_2$R10, —SR10, —S(O)R10, —S(O)$_2$R10, or —O($C_2$-$C_7$)alkenyl, —($C_1$-$C_3$)alkoxy (optionally substituted with 1 to 3 halogens), or —($C_1$-$C_6$)alkyl (optionally substituted with 1 to 3 halogens); and R10 is independently at each occurrence
- -hydrogen, or —($C_1$-$C_6$)alkyl (optionally substituted with 1 to 3 halogens).

2. A compound of claim 1, or a pharmaceutically acceptable salt thereof, wherein R1 and R2 are —H;

R3 is
- —($C_1$-$C_8$)alkyl (optionally substituted with 1 to 3 halogens), —($C_3$-$C_6$)cycloalkyl, —(C$_1$-C$_6$)alkyl-(C$_3$-C$_6$)cycloalkyl, or —(C$_3$-C$_6$)cycloalkyl-(C$_3$-C$_6$)alkyl (optionally substituted with 1 to 3 halogens);

R4 and R5 are independently
—H, -halogen, or —(C$_1$-C$_6$)alkyl (optionally substituted with 1 to 3 halogens);

R6 is

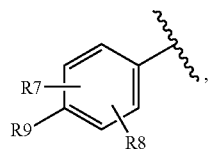

wherein the zig-zag mark shows the point of attachment to the parent molecule;

R7 and R8 are independently
—H, -halogen, —(C$_1$-C$_3$)allyl (optionally substituted with 1 to 3 halogens), or
—(C$_1$-C$_3$)alkoxy; and R9 is independently
—H, -halogen, or —(C$_1$-C$_6$) alkyl (optionally substituted with 1 to 3 halogens).

3. A compound of claim 1, or a pharmaceutically acceptable salt thereof, wherein
R1 and R2 are —H;
R3 is
—(C$_1$-C$_8$)alkyl (optionally substituted with 1 to 3 halogens), —(C$_3$-C$_6$)cycloalkyl,
—(C$_1$-C$_6$)alkyl-(C$_3$-C$_6$)cycloalkyl, or —(C$_3$-C$_6$)cycloalkyl-(C$_1$-C$_6$)alkyl (optionally substituted with 1 to 3 halogens);

R4 and R5 are independently
—H, -halogen, or —CH$_3$ (optionally substituted with 1 to 3 halogens);

R6 is

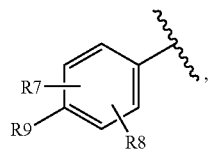

wherein the zig-zag mark shows the point of attachment to the parent molecule;
R7 and R8 are independently —H, or -halogen; and
R9 is independently —(C$_1$-C$_6$)alkyl (optionally substituted with 1 to 3 halogens).

4. The compound of claim 1, or a pharmaceutically acceptable salt thereof, wherein
R1 and R2 are —H; R3 is —(C$_1$-C$_8$)allyl (optionally substituted with 1 to 3 halogens),
—(C$_3$-C$_6$)cycloalkyl, —(C$_1$-C$_6$)alkyl-(C$_3$-C$_6$)cycloalkyl, or
—(C$_3$-C$_6$)cycloalkyl-(C$_1$-C$_6$)alkyl (optionally substituted with 1 to 3 halogens);
R4 and R5 are —CH$_3$ (optionally substituted with 1 to 3 halogens) and each occupies a position adjacent to R6 on the phenyl ring to which R6 is attached;
R6 is

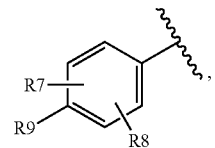

wherein the zig-zag mark shows the point of attachment to the parent molecule;
R7 and R8 are —H; and R9 is independently —(C$_1$-C$_6$) alkyl (optionally substituted with 1 to 3 halogens).

5. The compound of claim 1, or a pharmaceutically acceptable salt thereof, wherein
R1 and R2 are independently hydrogen or halogen; R3 is methyl, ethyl, propyl, isopropyl, butyl, pentyl, hexyl, heptyl, octyl, 3,3-dimethylbutyl, 2-methylpropyl, 3-methyl-butyl, tertbutyl, 4-methylpentyl, 2,2-dimethylpropyl, 3,3,3-trifluoropropyl, 4,4,4-trifluorobutyl, cyclopropyl, cyclobutyl, cyclopentyl, or cyclohexyl; R4 and R5 are independently hydrogen, methyl, ethyl, tertbutyl, cyclohexyl, pentyl, isopropoxy, chloro, fluoro, bromo, hydroxy, trifluoromethyl, —CN, methoxy, hydroxymethyl, 4-methylpentyloxy, or pentyloxy; R7 and R8 are independently hydrogen, fluoro, chloro, methyl, ethyl, pentyl, isopropyl, tertbutyl, trifluoromethyl, acetyl, 2-methylpropyl, methoxy, cyclohexyl, or trifluoromethoxy; and R9 is hydrogen, bromo, fluoro, methyl, tertbutyl, trifluoromethyl, or isopropyl.

6. The compound of claim 1, selected from the group consisting of formulae XI to XII;

| Formula Number | Structure |
|---|---|
| X1 | <img structure> |

-continued
| Formula Number | Structure |
|---|---|
| X2 | 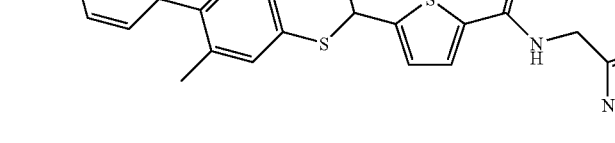 |
| X3 | 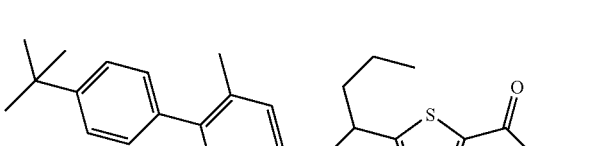 |
| X4 | 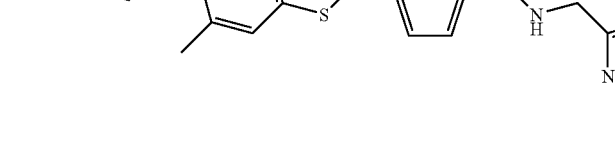 |
| X5 | 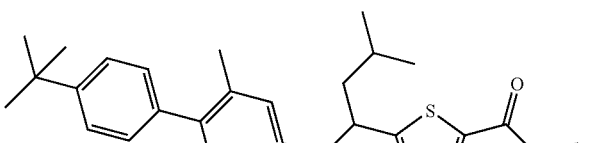 |
| X6 | 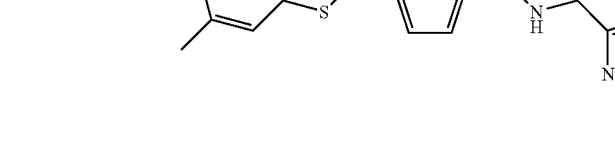 |
| X7 | 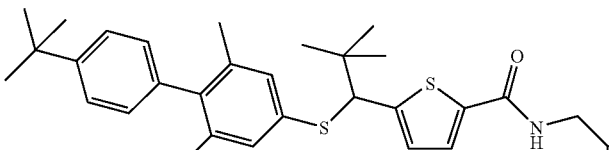 |

| Formula Number | Structure |
|---|---|
| X8 | 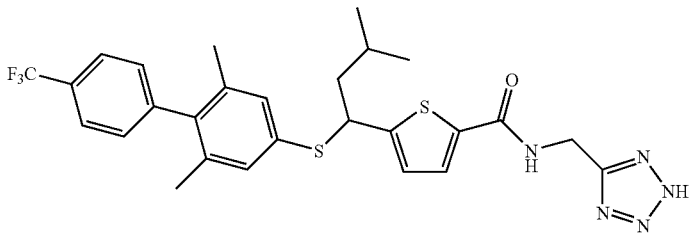 |
| X9 | 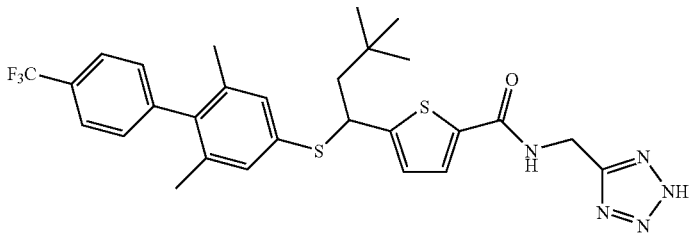 |
| X10 | 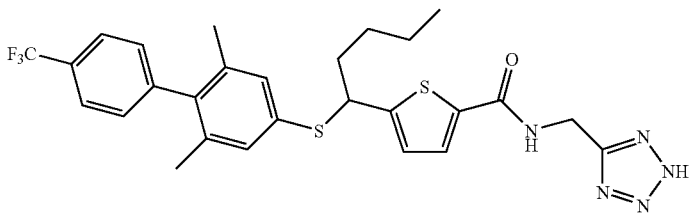 |
| X11 | 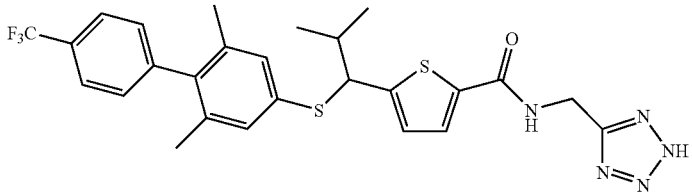 | or a pharmaceutically acceptable salt thereof.

7. A compound of claim 1 selected from the group consisting of
- (R,S)-5-[1-(4'-tert-Butyl-2,6-dimethyl-biphenyl-4-ylsulfanyl)-2-methyl-propyl]-thiophene-2-carboxylic acid (2H-tetrazol-5-ylmethyl)-amide;
- (±)-5-[1-(4'-tert-Butyl-2,6-dimethyl-biphenyl-4-ylsulfanyl)-propyl]-thiophene-2-carboxylic acid (2H-tetrazol-5-ylmethyl)-amide;
- (±)-5-[1-(4'-tert-Butyl-2,6-dimethyl-biphenyl-4-ylsulfanyl)-butyl]-thiophene-2-carboxylic acid (2H-tetrazol-5-ylmethyl)-amide;
- (±)-5-[1-(4'-tert-Butyl-2,6-dimethyl-biphenyl-4-ylsulfanyl)-pentyl]-thiophene-2-carboxylic acid (2H-tetrazol-5-ylmethyl)-amide;
- (±)-5-[1-(4'-tert-Butyl-2,6-dimethyl-biphenyl-4-ylsulfanyl)-3-methyl-butyl]-thiophene-2-carboxylic acid (2H-tetrazol-5-ylmethyl)-amide;
- ((±)-5-[1-(4'-tert-Butyl-2,6-dimethyl-biphenyl-4-ylsulfanyl)-3,3-dimethyl-butyl]-thiophene-2-carboxylic acid (2H-tetrazol-5-ylmethyl)-amide;
- (±)-5-[1-(4'-tert-Butyl-2,6-dimethyl-biphenyl-4-ylsulfanyl)-2,2-dimethyl-propyl]-thiophene-2-carboxylic acid (2H-tetrazol-5-ylmethyl)-amide;
- (±)-5-[1-(2,6-Dimethyl-4'-trifluoromethyl-biphenyl-4-ylsulfanyl)-butyl]-thiophene-2-carboxylic acid (1H-tetrazol-5-ylmethyl)-amide;
- (±)-5-[1-(2,6-Dimethyl-4'-trifluoromethyl-biphenyl-4-ylsulfanyl)-2-methyl-propyl]-thiophene-2-carboxylic acid (1H-tetrazol-5-ylmethyl)-amide;
- (±)-5-[1-(2,6-Dimethyl-4'-trifluoromethyl-biphenyl-4-ylsulfanyl)-2,2-dimethyl-propyl]-thiophene-2-carboxylic acid (1H-tetrazol-5-ylmethyl)-amide;
- (±)-5-[1-(2,6-Dimethyl-4'-trifluoromethyl-biphenyl-4-ylsulfanyl)-3-methyl-butyl]-thiophene-2-carboxylic acid (1H-tetrazol-5-ylmethyl)-amide;
- (±)-5-[1-(2,6-Dimethyl-4'-trifluoromethyl-biphenyl-4-ylsulfanyl)-3,3-dimethyl-butyl]-thiophene-2-carboxylic acid (1H-tetrazol-5-ylmethyl)-amide;
- (±) -5-[1-(2,6-Dimethyl-4'-trifluoromethyl-biphenyl-4-ylsulfanyl)-pentyl]-thiophene-2-carboxylic acid (1H-tetrazol-5-ylmethyl)-amide;
- 5-[1-(4'-tert-Butyl-2,6-dimethyl-biphenyl-4-ylsulfanyl)-2,2-dimethyl-propyl]-thiophene-2-carboxylic acid (2H-tetrazol-5-ylmethyl)-amide (Isomer 1);
- 5-[1-(4'-tert-Butyl-2,6-dimethyl-biphenyl-4-ylsulfanyl)-2,2-dimethyl-propyl]-thiophene-2-carboxylic acid (2H-tetrazol-5-ylmethyl)-amide (Isomer 2);

5-[1-(4'-tert-Butyl-2,6-dimethyl-biphenyl-4-ylsulfanyl)-propyl]-thiophene-2-carboxylic acid (2H-tetrazol-5-yl-methyl)-amide (Isomer 1);

5-[1-(4'-tert-Butyl-2,6-dimethyl-biphenyl-4-ylsulfanyl)-propyl]-thiophene-2-carboxylic acid (2H-tetrazol-5-yl-methyl)-amide (Isomer 2);

5-[1-(2,6-Dimethyl-4'-trifluoromethyl-biphenyl-4-ylsulfanyl)-butyl]-thiophene-2-carboxylic acid (1H-tetrazol-5-ylmethyl)-amide (Isomer 1);

5-[1-(2,6-Dimethyl-4'-trifluoromethyl-biphenyl-4-ylsulfanyl)-butyl]-thiophene-2-carboxylic acid (1H-tetrazol-5-ylmethyl)-amide (Isomer 2);

5-[1-(2,6-Dimethyl-4'-trifluoromethyl-biphenyl-4-ylsulfanyl)-2-methyl-propyl]-thiophene-2-carboxylic acid (1H-tetrazol-5-ylmethyl)-amide (Isomer 1);

5-[1-(2,6-Dimethyl-4'-trifluoromethyl-biphenyl-4-ylsulfanyl)-2-methyl-propyl]-thiophene-2-carboxylic acid (1H-tetrazol-5-ylmethyl)-amide (Isomer 2);

5-[1-(2,6-Dimethyl-4'-trifluoromethyl-biphenyl-4-ylsulfanyl)-2,2-dimethyl-propyl]-thiophene-2-carboxylic acid (1H-tetrazol-5-ylmethyl)-amideb (Isomer 1);

5-[1-(2,6-Dimethyl-4'-trifluoromethyl-biphenyl sulfanyl)-2,2-dimethyl-propyl]-thiophene-2-carboxylic acid (1H-tetrazol-5-ylmethyl)-amideb (Isomer 2);

5-[1-(2,6-Dimethyl-4'-trifluoromethyl-biphenyl-4-ylsulfanyl)-3-methyl-butyl]-thiophene-2-carboxylic acid (1H-tetrazol-5-ylmethyl)-amide (Isomer 1);

5-[1-(2,6-Dimethyl-4'-trifluoromethyl-biphenyl-4-ylsulfanyl)-3-methyl-butyl]-thiophene-2-carboxylic acid (1H-tetrazol-5-ylmethyl)-amide (Isomer 2);

5-[1-(2,6-Dimethyl-4'-trifluoromethyl-biphenyl-4-ylsulfanyl)-3,3-dimethyl-butyl]-thiophene-2-carboxylic acid (1H-tetrazol-5-ylmethyl)-amide (Isomer 1);

5-[1-(2,6-Dimethyl-4'-trifluoromethyl-biphenyl-4-ylsulfanyl)-3,3-dimethyl-butyl]-thiophene-2-carboxylic acid (1H-tetrazol-5-ylmethyl)-amide (Isomer 2);

5-[1-(2,6-Dimethyl-4'-trifluoromethyl-biphenyl-4-ylsulfanyl)-pentyl]-thiophene-2-carboxylic acid (1H-tetrazol-5-ylmethyl)-amide (Isomer 1); and 5-[1-(2,6-Dimethyl-4'-trifluoromethyl-biphenyl-4-ylsulfanyl)-pentyl]-thiophene-2-carboxylic acid (1H-tetrazol-5-ylmethyl)-amide (Isomer 2);

or a pharmaceutically acceptable salt thereof.

8. A pharmaceutical composition which comprises a compound or salt of claim 1 and a pharmaceutically acceptable carrier.

* * * * *